United States Patent
Hajati

(10) Patent No.: US 10,589,317 B2
(45) Date of Patent: Mar. 17, 2020

(54) MICROMACHINED ULTRASONIC TRANSDUCER ARRAYS WITH MULTIPLE HARMONIC MODES

(71) Applicant: Arman Hajati, Santa Clara, CA (US)

(72) Inventor: Arman Hajati, Santa Clara, CA (US)

(73) Assignee: FUJIFILM DIMATIX, INC., Lebanon, NH (US)

( * ) Notice: Subject to any disclaimer, the term of this patent is extended or adjusted under 35 U.S.C. 154(b) by 309 days.

(21) Appl. No.: 15/486,238

(22) Filed: Apr. 12, 2017

(65) Prior Publication Data

US 2017/0216883 A1 Aug. 3, 2017

Related U.S. Application Data

(62) Division of application No. 13/830,251, filed on Mar. 14, 2013, now Pat. No. 9,660,170.
(Continued)

(51) Int. Cl.
*B06B 1/06* (2006.01)
*B06B 1/02* (2006.01)
(Continued)

(52) U.S. Cl.
CPC .......... *B06B 1/0276* (2013.01); *A61B 18/082* (2013.01); *B06B 1/0622* (2013.01);
(Continued)

(58) Field of Classification Search
CPC ....... B06B 1/06; B06B 1/0603; B06B 1/0607; B06B 1/0622; B06B 1/0625;
(Continued)

(56) References Cited

U.S. PATENT DOCUMENTS

| 4,398,116 A | 8/1983 | Lewis |
| 4,725,994 A | 2/1988 | Kaneko et al. |
| (Continued) | | |

FOREIGN PATENT DOCUMENTS

| CN | 101084586 | 12/2007 |
| CN | 101262960 | 9/2008 |
| (Continued) | | |

OTHER PUBLICATIONS

Fourth Notification of Office Action for Chinese Application No. 201380023369.8 dated Jul. 20, 2017, 8 pages.
(Continued)

*Primary Examiner* — Derek J Rosenau
(74) *Attorney, Agent, or Firm* — Womble Bond Dickinson (US) LLP

(57) ABSTRACT

Micromachined ultrasonic transducer (MUT) arrays capable of multiple resonant modes and techniques for operating them are described, for example to achieve both high frequency and low frequency operation in a same device. In embodiments, various sizes of piezoelectric membranes are fabricated for tuning resonance frequency across the membranes. The variously sized piezoelectric membranes are gradually transitioned across a length of the substrate to mitigate destructive interference between membranes oscillating in different modes and frequencies.

4 Claims, 15 Drawing Sheets

Related U.S. Application Data

(60) Provisional application No. 61/718,952, filed on Oct. 26, 2012.

(51) Int. Cl.
| | | |
|---|---|---|
| *H01L 41/04* | (2006.01) | |
| *H01L 41/08* | (2006.01) | |
| *H01L 41/331* | (2013.01) | |
| *A61B 18/08* | (2006.01) | |

(52) U.S. Cl.
CPC .......... *B06B 1/0629* (2013.01); *H01L 41/042* (2013.01); *H01L 41/0825* (2013.01); *H01L 41/331* (2013.01)

(58) Field of Classification Search
CPC ... B06B 1/0629; B06B 1/0688; B06B 1/0692; B06B 1/0696
USPC ........................................ 310/317, 322, 334
See application file for complete search history.

(56) References Cited

U.S. PATENT DOCUMENTS

| | | |
|---|---|---|
| 5,115,810 A | 5/1992 | Wantanabe et al. |
| 5,969,621 A | 10/1999 | Getman et al. |
| 6,262,946 B1 | 7/2001 | Khuri-Yakub et al. |
| 6,262,964 B1 | 7/2001 | Yakota et al. |
| 7,477,572 B2 | 1/2009 | Caronti et al. |
| 7,646,133 B2 | 1/2010 | Degertekin |
| 7,652,410 B2 | 1/2010 | Prus |
| 7,727,156 B2 | 6/2010 | Angelsen et al. |
| 7,728,487 B2 | 6/2010 | Adachi et al. |
| 7,902,722 B2 | 3/2011 | Vilkomerson |
| 7,982,362 B2 | 7/2011 | Adachi et al. |
| 8,327,711 B2 | 12/2012 | Kasai et al. |
| 8,767,512 B2 | 7/2014 | Hajati |
| 8,861,753 B2 | 10/2014 | Kasai et al. |
| 9,061,320 B2 | 6/2015 | Hajati et al. |
| 9,070,861 B2 | 6/2015 | Bibl et al. |
| 9,070,862 B2 | 6/2015 | Bibl et al. |
| 9,074,985 B2 | 7/2015 | Lebental et al. |
| 9,454,954 B2 | 9/2016 | Hajati |
| 2002/0115198 A1 | 8/2002 | Nerenberg et al. |
| 2003/0137224 A1 | 7/2003 | Zloter et al. |
| 2004/0174773 A1 | 9/2004 | Thomenius et al. |
| 2004/0190377 A1 | 9/2004 | Lewandowski et al. |
| 2005/0203397 A1 | 9/2005 | Degertekin |
| 2007/0035204 A1 | 2/2007 | Angelsen et al. |
| 2007/0059858 A1 | 3/2007 | Caronti et al. |
| 2007/0164631 A1 | 7/2007 | Adachi et al. |
| 2007/0164632 A1 | 7/2007 | Adachi et al. |
| 2007/0167814 A1 | 7/2007 | Wakabayashi et al. |
| 2007/0193354 A1 | 8/2007 | Felix et al. |
| 2008/0013405 A1* | 1/2008 | Moon ................... B06B 1/0629 367/92 |
| 2009/0001853 A1 | 1/2009 | Adachi et al. |
| 2009/0161490 A1 | 6/2009 | Wall et al. |
| 2009/0163129 A1 | 6/2009 | Durjan et al. |
| 2009/0182237 A1 | 7/2009 | Angelsen et al. |
| 2009/0204001 A1 | 8/2009 | Ona et al. |
| 2009/0301200 A1 | 12/2009 | Tanaka et al. |
| 2010/0168583 A1 | 7/2010 | Dausch et al. |
| 2010/0174195 A1 | 7/2010 | Haider et al. |
| 2010/0201222 A1 | 8/2010 | Adachi et al. |
| 2010/0207485 A1 | 8/2010 | Dirksen et al. |
| 2010/0212432 A1 | 8/2010 | Kasai et al. |
| 2010/0268058 A1 | 10/2010 | Chen |
| 2010/0277040 A1 | 11/2010 | Klee et al. |
| 2010/0327695 A1 | 12/2010 | Goel et al. |
| 2011/0057541 A1 | 3/2011 | Kyung-Il et al. |
| 2011/0074248 A1 | 3/2011 | Hishinuma |
| 2011/0272693 A1 | 11/2011 | Kobayashi et al. |
| 2012/0086307 A1 | 4/2012 | Kandori et al. |
| 2012/0176002 A1 | 7/2012 | Kim et al. |
| 2012/0206014 A1 | 8/2012 | Bibl et al. |
| 2013/0070942 A1 | 3/2013 | Kasai et al. |
| 2013/0208572 A1 | 8/2013 | Klee et al. |
| 2013/0293065 A1 | 11/2013 | Hajati |
| 2013/0294201 A1 | 11/2013 | Hajati |
| 2013/0294202 A1 | 11/2013 | Hajati |
| 2013/0294622 A1 | 11/2013 | Kasai et al. |
| 2014/0117812 A1 | 5/2014 | Hajati |

FOREIGN PATENT DOCUMENTS

| | | |
|---|---|---|
| CN | 101583062 | 11/2009 |
| CN | 201993187 | 9/2011 |
| CN | 102305627 | 1/2012 |
| CN | 102595287 | 7/2012 |
| EP | 1764162 | 3/2007 |
| EP | 2110186 | 10/2009 |
| EP | 2130495 | 12/2009 |
| JP | 2006075425 | 3/2006 |
| JP | 2008118168 A | 5/2008 |
| JP | 2009026723 | 5/2009 |
| JP | 2010165341 | 7/2010 |
| JP | 2011071842 | 4/2011 |
| WO | WO-0225630 | 3/2002 |
| WO | WO-2004016036 | 2/2004 |
| WO | WO-2007013814 | 1/2007 |
| WO | WO-2011094393 | 8/2011 |
| WO | WO-2013165705 | 11/2013 |

OTHER PUBLICATIONS

Second Notification of Office Action for Chinese Patent Application No. 201380055935.3 dated Jan. 11, 2018, 6 pages.
Third Notification of Office Action for Chinese Patent Application No. 201380055935.3, dated Jun. 19, 2018, 5 pages.
Office Action for Japanese Patent Application No. JP 2015-539616, dated Jun. 5, 2017, 6 pages.
Notice of Allowance from U.S. Appl. No. 13/648,225 dated Feb. 18, 2015, 11 pgs.
Non-Final Office Action from U.S. Appl. No. 13/648,225 dated Oct. 24, 2014, 19 pgs.
Non-Final Office Action from Chinese Patent Application No. 201380023381.9 dated Dec. 23, 2015, 7 pgs.
Second Office Action from Chinese Patent Application No. 201380023381.9 dated Aug. 19, 2016, 12 pgs.
International Preliminary Report on Patentability from PCT/US2013/037419 dated Nov. 13, 2014, 13 pgs.
International Search Report and Written Opinion from PCT/US2013/037419 dated Mar. 28, 2014, 18 pgs.
Notice of Allowance from U.S. Appl. No. 13/830,288 dated Feb. 2, 2016, 7 pgs.
Notice of Allowance from U.S. Appl. No. 13/830,288 dated May 24, 2016, 5 pgs.
Non-Final Office Action from U.S. Appl. No. 13/830,288 dated Sep. 25, 2017, 14 pgs.
First Office Action from Chinese Patent Application No. 201380023320.2 dated Jan. 29, 2016, 21 pgs.
Second Office Action from Chinese Patent Application No. 201380023320.2 dated Aug. 23, 2016, 9 pgs.
Third Office Action from Chinese Patent Application No. 201380023320.2 dated Feb. 3, 2017, 10 pgs.
Non-Final Office Action from Japanese Patent Application No. 2015-510308 dated Feb. 22, 2017, 3 pgs.
International Preliminary Report on Patentability from PCT/US2013/037379 dated Nov. 13, 2014, 8 pgs.
International Search Report and Written Opinion from PCT/US2013/037379 dated Dec. 13, 2013, 11 pgs.
Notice of Allowance from U.S. Appl. No. 13/835,500 dated Feb. 18, 2014, 5 pgs.
Corrected Notice of Allowability from U.S. Appl. No. 13/835,500 dated May 7, 2014, 7 pgs.
Non-Final Office Action from U.S. Appl. No. 13/835,500 dated Sep. 26, 2013, 12 pgs.

(56) References Cited

OTHER PUBLICATIONS

Notice of Allowance from U.S. Appl. No. 14/289,139 dated Dec. 20, 2016, 13 pgs.
First Office Action from Chinese Patent Application No. 201380023369.8 dated Feb. 22, 2016, 19 pgs.
Second Office Action from Chinese Patent Application No. 201380023369.8 dated Sep. 26, 2016, 22 pgs.
Non-Final Office Action from Japanese Patent Application No. 2015-510309 dated Mar. 23, 2017, 18 pgs.
International Preliminary Report on Patentability from PCT/US2013/037382 dated Nov. 13, 2014, 6 pgs.
International Search Report and Written Opinion from PCT/US2013/037382 dated Feb. 4, 2014, 8 pgs.
Non-Final Office Action from U.S. Appl. No. 13/830,251 dated Jul. 16, 2015, 16 pgs.
Final Office Action from U.S. Appl. No. 13/860,251 dated Dec. 31, 2015, 12 pgs.
Non-Final Office Action from U.S. Appl. No. 13/830,251 dated Apr. 20, 2016, 17 pgs.
Final Office Action from U.S. Appl. No. 13/860,251 dated Sep. 29, 2016, 16 pgs.
Notice of Allowance from U.S. Appl. No. 13/860,251 dated Feb. 8, 2017, 9 pgs.
Extended European Search Report from European Patent Application No. 13848357.3 dated May 27, 2016, 9 pgs.
International Preliminary Report on Patentability from PCT/US2013/063255 dated May 7, 2015, 9 pgs.
International Search Report and Written Opinion from PCT/US2013/63255 dated Feb. 7, 2014, 17 pgs.
First Office Action from Chinese Patent Application No. 201380055935.3 dated May 2, 2017, 27 pgs.

* cited by examiner

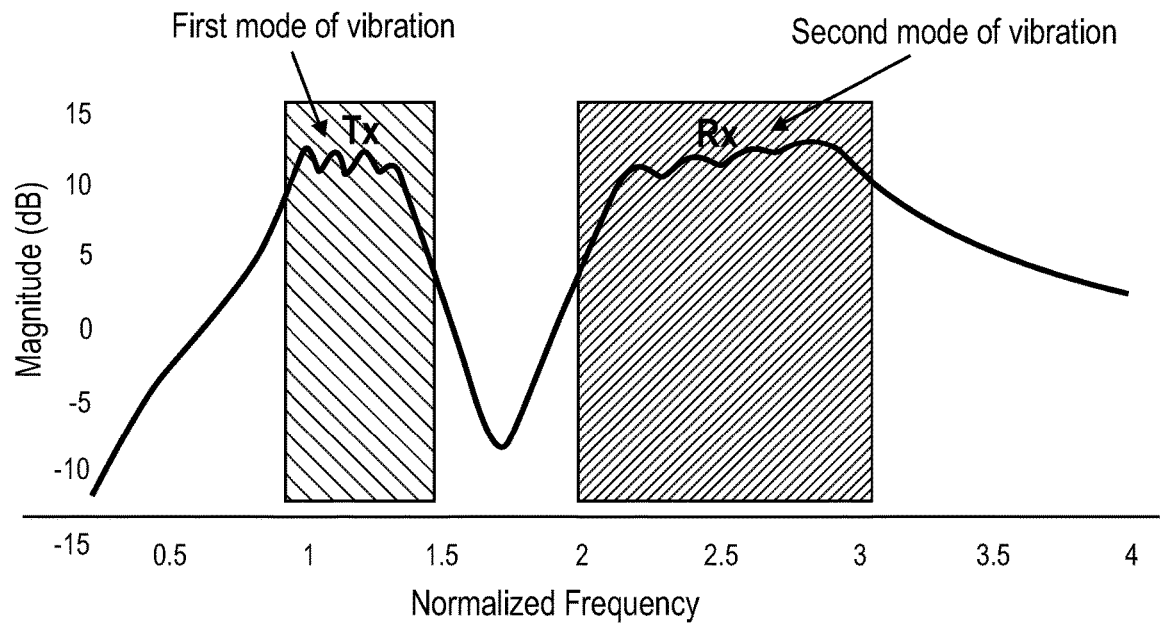
FIG. 8A
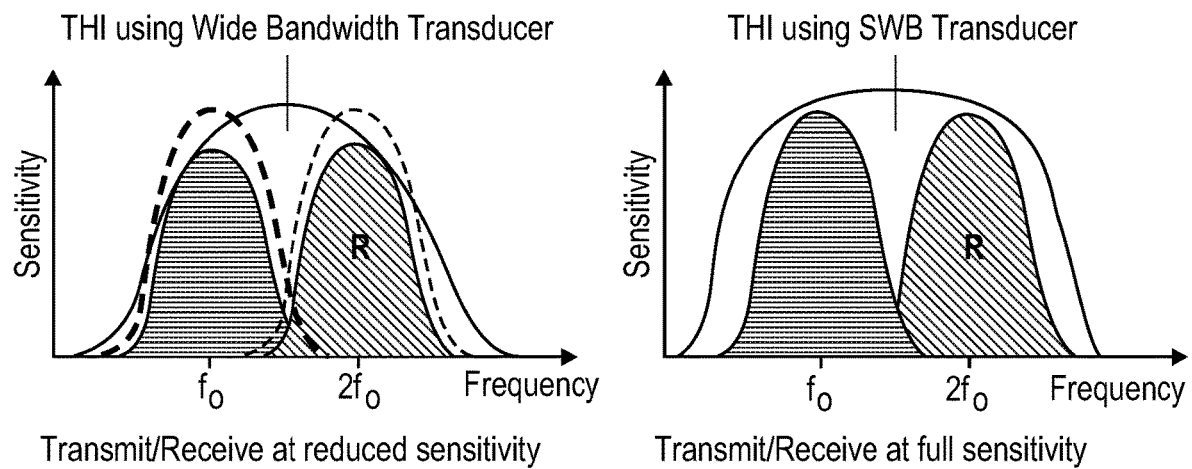
FIG. 8B          FIG. 8C

MICROMACHINED ULTRASONIC TRANSDUCER ARRAYS WITH MULTIPLE HARMONIC MODES

CROSS-REFERENCE TO RELATED APPLICATIONS

This application is a Divisional of U.S. patent application No. Ser. 13/860,251, filed on Mar. 14, 2013, which claims priority to the U.S. provisional utility patent application titled "PIEZOELECTRIC TRANSDUCER ARRAYS WITH $1^{ST}$ AND $2^{ND}$ HARMONIC MODES," filed on Oct. 26, 2012 and having application No. 61/718,952, the entire contents of which are incorporated herein by reference for all purposes.

This application is related to the U.S. utility patent application titled "ULTRA WIDE BANDWIDTH PIEZOELECTRIC TRANSDUCER ARRAYS," filed on Oct. 9, 2012 and having application Ser. No. 13/648,225.

TECHNICAL FIELD

Embodiments of the invention generally relate to ultrasonic transducers, and more specifically pertain to micromachined ultrasonic transducer (MUT) arrays.

BACKGROUND

An ultrasonic transducer device typically includes a membrane capable of vibrating in response to a time-varying driving voltage to generate a high frequency pressure wave in a propagation medium (e.g., air, water, or body tissue) in contact with an exposed outer surface of the transducer element. This high frequency pressure wave can propagate into other media. The same membrane can also receive reflected pressure waves from the propagation media and convert the received pressure waves into electrical signals. The electrical signals can be processed in conjunction with the driving voltage signals to obtain information on variations of density or elastic modulus in the propagation media.

Piezoelectric and capacitive transducer devices have proven useful in the imaging field. While many ultrasonic transducer devices that use piezoelectric membranes are formed by mechanically dicing a bulk piezoelectric material or by injection molding a carrier material infused with piezoelectric ceramic crystals, devices can be advantageously fabricated inexpensively to exceedingly high dimensional tolerances using various micromachining techniques (e.g., material deposition, lithographic patterning, feature formation by etching, etc.). As such, large arrays of transducer elements may be employed with individual ones of the arrays driven via beam forming algorithms. Such arrayed devices are known as piezoelectric MUT (pMUT) arrays. Capacitive transducers may also be similarly micromachined as capacitive MUT (cMUT) arrays.

One issue with conventional MUT arrays is that the bandwidth, being a function of the real acoustic pressure exerted from the transmission medium, may be limited. Because ultrasonic transducer applications, such as fetal heart monitoring and arterial monitoring, span a wide range of frequencies (e.g., lower frequencies providing relatively deeper imaging capability and higher frequencies providing shallower imaging capability), axial resolution (i.e. the resolution in the direction parallel to the ultrasound beam) would be advantageously improved by shortening the pulse length via enhancing the bandwidth of a MUT array.

Another issue with conventional pMUT arrays is that the mechanical coupling through the vibration of the substrate and the acoustic coupling between close elements found in a pMUT array can lead to undesirable crosstalk between transducer elements. Signal to noise ratios in the ultrasonic transducer applications would be advantageously improved by reducing undesirable forms of crosstalk within such pMUT arrays.

SUMMARY

In an embodiment, a transducer element population of a MUT array is configured for multiple modes of oscillation. These multiple modes include at least a first and second resonant mode, and may further include third, forth, and higher modes. Such multi-resonant mode, or multi-harmonic mode, MUT arrays are referred to herein simply as "multi-mode" MUT arrays. In embodiments, harmonics are made in-phase through dimensioning of membrane sizes and arranging the membranes of differing size to mitigate or avoid destructive interaction between proximate membranes within a channel, or crosstalk between proximate channels.

In embodiments, a multi-mode MUT array is operated with the entire bandwidth associated with the multiple resonant modes employed in both sending and receiving modes of an ultrasonic transducer to achieve a super-wide bandwidth. For such embodiments, membranes are sized and driven with an electrical signal to induce a first order mode of vibration that has a frequency band that overlaps with that associated predominantly with the second order mode of vibration.

In embodiments, a multi-mode MUT array is operated with bandwidth associated with the multiple resonant modes apportioned between sending and receiving modes of an ultrasonic transducer. In one such embodiment, a first order mode of vibration suitable as a transmission band is induced by a drive signal and a frequencies associated with a second order mode of vibration suitable as a reception band are filtered by a signal receiver. With proper tuning of membrane size(s), for example, the technique of tissue harmonic imaging (THI) may be performed using a first band of lower frequency vibration and a second band of higher frequency vibration without suffering the limitations in gain typical of lower bandwidth transducers.

In embodiments, a multi-mode MUT array is operated with bandwidth associated with the multiple resonant modes apportioned across different channels of an ultrasonic transducer. A first frequency band associated with one or more modes of vibration is driven in a first channel of the transducer while a second frequency band associated with one or more other mode is driven in a second channel to achieve a high sampling rate. In certain such embodiments, the ultrasonic transducer is operative with multiple focus zones concurrently, during which a low frequency (first mode) channel focuses at a deeper focus length than a high frequency (second mode) channel.

In embodiments, dimensioning of membrane sizes and arranging the membranes of differing size spatially over a substrate is achieved, at least in part, through one or more sensitivity analysis. Because harmonic phasing is a complex function sensitive to many factors, this challenge is at least partially addressed by optimizing a frequency response of a MUT array from a modeled nominal dimension. In certain advantageous piezoelectric embodiments, the sensitivity analysis is performed at a single mask level that defines an area of contact between an electrode and a piezoelectric material of the transducer membrane. In certain such embodiments, a single pMUT array is fabricated with the sensitivity analysis performed across different channels of the array. Channel responses are then measured and compared to nominal to deduce optimal sizing for each membrane size classification. A final mask set is then defined based on the optimal mask dimension for each different membrane size employed in the array.

BRIEF DESCRIPTION OF THE DRAWINGS

Embodiments of the present invention are illustrated by way of example, and not by way of limitation, and can be more fully understood with reference to the following detailed description when considered in connection with the figures, in which:

FIG. 8A is modeled frequency response showing two bands corresponding to first and second vibrational modes of a PMUT array suitable for separate transmit and receive modes of an ultrasonic transducer, in accordance with an embodiment;

FIGS. 8B and 8C illustrate an effect of apportioning multi-mode MUT array bandwidth for tissue harmonic imaging (THI) on response sensitivity;

DETAILED DESCRIPTION

Figure 1A:
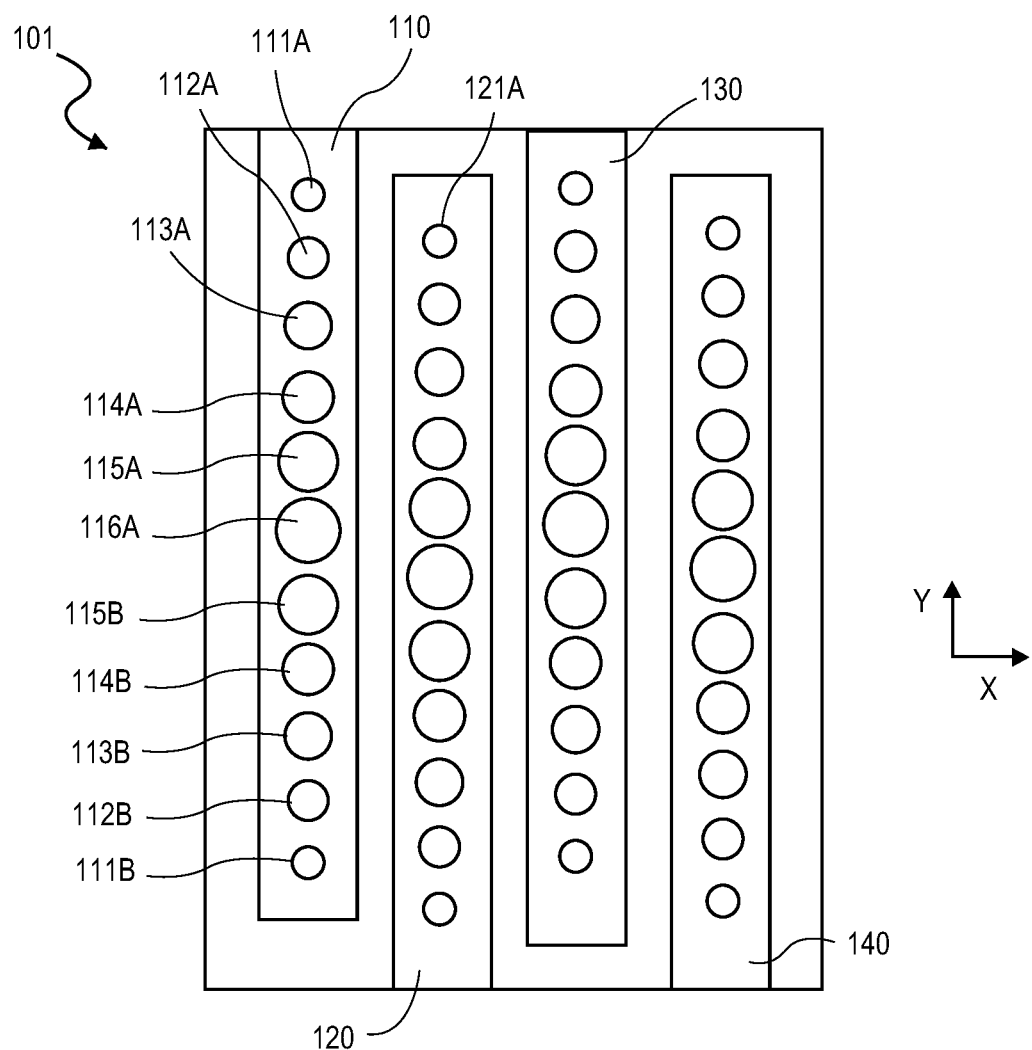
FIGS. 1A and 1B are plan views of multi-mode MUT arrays with circular transducer elements, in accordance with an embodiment.

In the following description, numerous details are set forth, however, it will be apparent to one skilled in the art, that the present invention may be practiced without these specific details. In some instances, well-known methods and devices are shown in block diagram form, rather than in detail, to avoid obscuring the present invention. Reference throughout this specification to "an embodiment" means that a particular feature, structure, function, or characteristic described in connection with the embodiment is included in at least one embodiment of the invention. Thus, the appearances of the phrase "in an embodiment" in various places throughout this specification are not necessarily referring to the same embodiment of the invention. Furthermore, the particular features, structures, functions, or characteristics may be combined in any suitable manner in one or more embodiments. For example, a first embodiment may be combined with a second embodiment anywhere the two embodiments are not specifically denoted as being mutually exclusive.

The term "coupled" is used herein to describe functional or structural relationships between components. "Coupled" may be used to indicated that two or more elements are in either direct or indirect (with other intervening elements between them or through the medium) mechanical, acoustic, optical, or electrical contact with each other, and/or that the two or more elements co-operate or interact with each other (e.g., as in a cause and effect relationship).

The terms "over," "under," "between," and "on" as used herein refer to a relative position of one component or material layer with respect to other components or layers where such physical relationships are noteworthy for mechanical components in the context of an assembly, or in the context of material layers of a micromachined stack. One layer (component) disposed over or under another layer (component) may be directly in contact with the other layer (component) or may have one or more intervening layers (components). Moreover, one layer (component) disposed between two layers (components) may be directly in contact with the two layers (components) or may have one or more intervening layers (components). In contrast, a first layer (component) "on" a second layer (component) is in direct contact with that second layer (component).

The singular forms "a", "an" and "the" are intended to include the plural forms as well, unless the context clearly indicates otherwise. It will also be understood that the term "and/or" as used herein refers to and encompasses any and all possible combinations of one or more of the associated listed items.

In an embodiment, a piezoelectric transducer element population of a MUT array is configured for multiple modes of oscillation. Each mode corresponds to a solutions of Bessel functions for a given membrane geometry and include at least a first and second resonant mode, and may further include third, forth, and higher resonant modes of the transducer membrane. More than one resonant mode poses challenges because coupling (e.g., through the transmission media and/or mechanical connections to the substrate, etc.) between transducer elements oscillating in different modes can result in destructive interaction, which is generally a result of the harmonic modes being out of phase. In embodiments herein, membranes of a particular channel are both dimensioned and spatially arranged so as to mitigate such destructive interaction between membranes within a channel, or crosstalk between proximate channels, when multiple modes of oscillation are present.

Figure 1B:
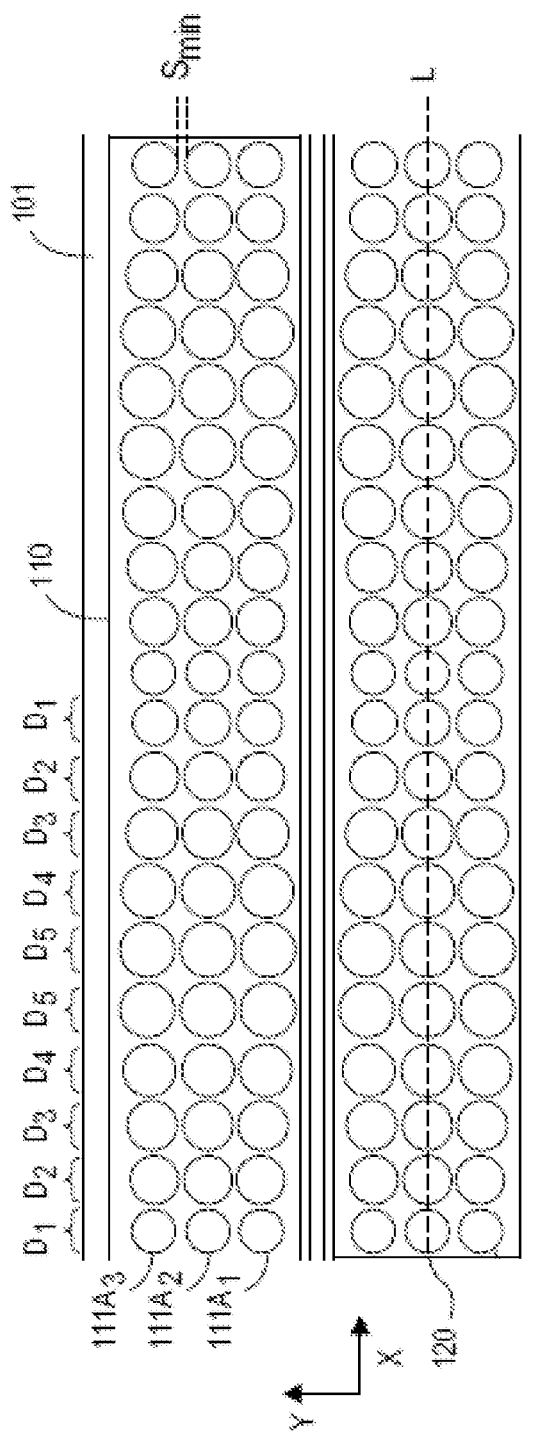

FIGS. 1A and 1B are plan views of multi-mode MUT arrays with circular transducer elements. FIG. 1A is a plan view of a MUT array 101, in accordance with an embodiment. The array 101 includes a plurality of electrode rails 110, 120, 130, 140 disposed over an area defined by a first dimension, x and a second dimension y, of a substrate 101. Each of the drive/sense electrode rails (e.g., 110) is electrically addressable independently from any other drive/sense electrode rails (e.g., 120 or 130) and are functionally, separate channels of the array 101. Each channel has a characteristic frequency response that is a composite of the responses from individual transducer elements within the channel. A drive/sense electrode for each channel is electrically coupled in parallel to each element. For example in FIG. 1A, transducer elements 111A-116A and 111B-116B are coupled together to be electrically driven by the drive/sense electrode rail 110. Similarly, transducer elements (e.g., including transducer element 121A) are all coupled together in parallel to the drive/sense electrode rail 120. Generally, any number of transducer elements may lumped together within a channel, as a function of the membrane diameter, element pitch and substrate area allocated for each channel For the embodiment in FIG. 1B, for example, each channel includes three adjacent elements in a first (y) dimension (e.g., elements $111A_1$, $111A_2$, and $111A_3$). Within this first dimension, all elements have the same membrane size (i.e., same diameter).

In an embodiment, at least one membrane dimension varies across elements of a same channel of the apparatus. As shown in FIGS. 1A and 1B, the circular membrane diameters vary along at least one dimension of the substrate (e.g., y-dimension) such that each channel includes a range of membrane sizes. In the depicted embodiments, each channel includes the same number of membranes of a particular size and a same number of different sizes. As resonance frequency is a function of membrane size (with a higher frequency associated with smaller membrane size), when a given electrical drive signal is applied to a channel, a particular frequency response is induced, or when a given frequency response is returned through a media, it generates a particular electrical sense signal. For the embodiments depicted in FIGS. 1A and 1B where each channel has the same population of elements (same number and size distribution), and a same spatial layout, each channel can be expected to have very nearly the same frequency response. Alternatively, channels with differing element populations (i.e., a different number of membrane sizes, different number of membranes of a particular size, or different spatial arrangements over the substrate) can be expected to have significantly different frequency responses.

In embodiments, the membranes of differing size within a given channel are spatially arranged on the substrate to avoid destructive interaction between the membranes. It has been found that varying membrane size in a continuous, smooth, and/or incremental manner over one or more substrate dimension advantageously reduces destructive interaction stemming from phase mismatch between membranes of drastically different size. In embodiments, resonance phase is maintained across the element population with nearest neighboring elements having similar sized membranes such that the change in membrane size over a given distance does not exceed a particular threshold (e.g., less than 10% change in circular membrane diameter between nearest neighbors, advantageously less than 5%, and most advantageously less than 2%). This approach ensures that every element is surrounded by resonators with similar enough resonance frequency (and therefore phase spectrum) to avoid a destructive interaction. Too drastic of a change in membrane size can result in a phase relationship between adjacent membranes that induces a notch in the frequency response of the channel. For example, the action of an aggressor/offender membrane may locally push, or pile up, the transmission media over the victim membrane (e.g., a nearest neighbor or otherwise proximal to the offender), increasing effective membrane mass of the second membrane at inopportune times with respect to the victim membrane's phase and thereby dampen or retard performance of the victim element. If such acoustic dampening (or transmission media dampening) is severe, an undesirable zero crossing can occur under operating conditions inducing multiple modes of oscillation.

As depicted in FIG. 1A, transducer element 111A a first size (e.g., smallest diameter membrane) is adjacent to element 112A of a second size (e.g., next larger diameter membrane) with the membrane size gradually increasing in a step-wise manner through a first series of elements with ever increasing membrane size (e.g., 114A, 115A, 116A) and then a second series with stepwise decreasing size back to the smallest diameter. As shown in FIG. 1B, membrane diameter similarly increases incrementally from $D_1$, $D_2$, $D_3$, $D_4$, and $D_5$, and then decreases incrementally from a second membrane with radius $D_5$, to a second with $D_4$, etc., back down to a second membrane with $D_1$. The set of membranes consecutively spanning the diameters $D_1$-$D_5$, and $D_5$-$D_1$ forms a repeating unit (RU) that is continued over the length of the channel in the x-dimension. Both of the spatial arrangements depicted in FIG. 1A and FIG. 1B ensure each element with the channel population is adjacent to another element of the same size or of a next smallest or next largest size for any number of different membrane sizes (e.g., three, four, or five different sizes depicted in FIG. 1B, etc.). However, unlike the embodiment in FIG. 1A, which has only one membrane of maximum dimension (116A), the spatial density of all membrane sizes within the RU of FIG. 1B is advantageously equal with two membranes of every size, or "type."

Figure 1C:
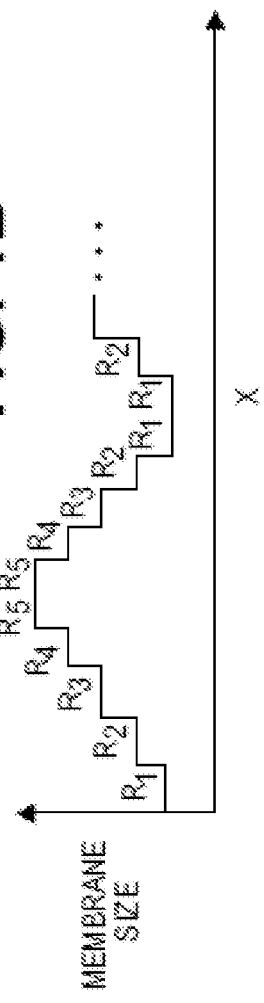
FIG. 1C is a graph depicting a one-dimensional spatial arrangement of transducer membrane sizes, in accordance with an embodiment of a multi-mode MUT array.

In the illustrated embodiments, transducer element membrane size within a channel of an array is a cyclic function of at least one dimension of the substrate. FIG. 1C is a graph depicting a generalized one-dimensional spatial arrangement of transducer membrane sizes that follows a cyclic function, in accordance with an embodiment of a multi-mode MUT array. The frequency of the cyclic size variation is limited by the phase matching particular to the mechanical characteristics of the MUT as well as the transmission media and therefore may vary with implementation. In certain embodiments, the amplitude of the cyclic function associated with the maximum and minimum size of the membranes is sufficiently large that the difference between the membranes of maximum and minimum size within the RU is larger than the difference in size between any two adjacent membranes. As one example, the range between largest and smallest membrane size may be selected to ensure at least two modes of oscillation are induced within the RU by one or more given electrical drive signal while the increment in size between adjacent membranes may be selected to ensure all transducer elements contribute to a response curve maintaining a 3 dB bandwidth. Corresponding minimum and maximum membrane sizes would then have at least both a $1^{st}$ and $2^{nd}$ order harmonic (and potentially $3^{rd}$ and higher orders to a lesser extent) induced within a channel. As one example, a range of 20-150 µm would be typical of membrane dimensions for MHz frequency responses from a transducer having the general structure described in the context of FIGS. 2A-2C, and an increment of 1-10 µm would typically provide sufficient response overlap. Thus, for the embodiment illustrated in FIG. 1B, the five membrane sizes could correspond to diameters cycling between 100 and 140 µm in increments of 10 µm.

FIG. 1B further illustrates a multiplicity of membranes of one size arrayed in a second dimension of the substrate (e.g., y-dimension where membranes $111A_1$, $111A_2$ and $111A_3$ are all of the same diameter). The embodiment depicted in FIG. 1B provides an advantageously higher fill factor than the embodiment depicted in FIG. 1A and concomitantly higher gain as the spatial density of each membrane size is greater in FIG. 1B. As also shown in FIG. 1B, a same minimum space $S_{min}$ is maintained between membranes of a same size, regardless of their size. A center row of the membranes in the channel (e.g., membrane $111A_2$ have their centers aligned on the channel axis L with centers of the adjacent membrane rows being one diameter plus one minimum space $S_{min}$ from the channel axis L.

Figure 1D:
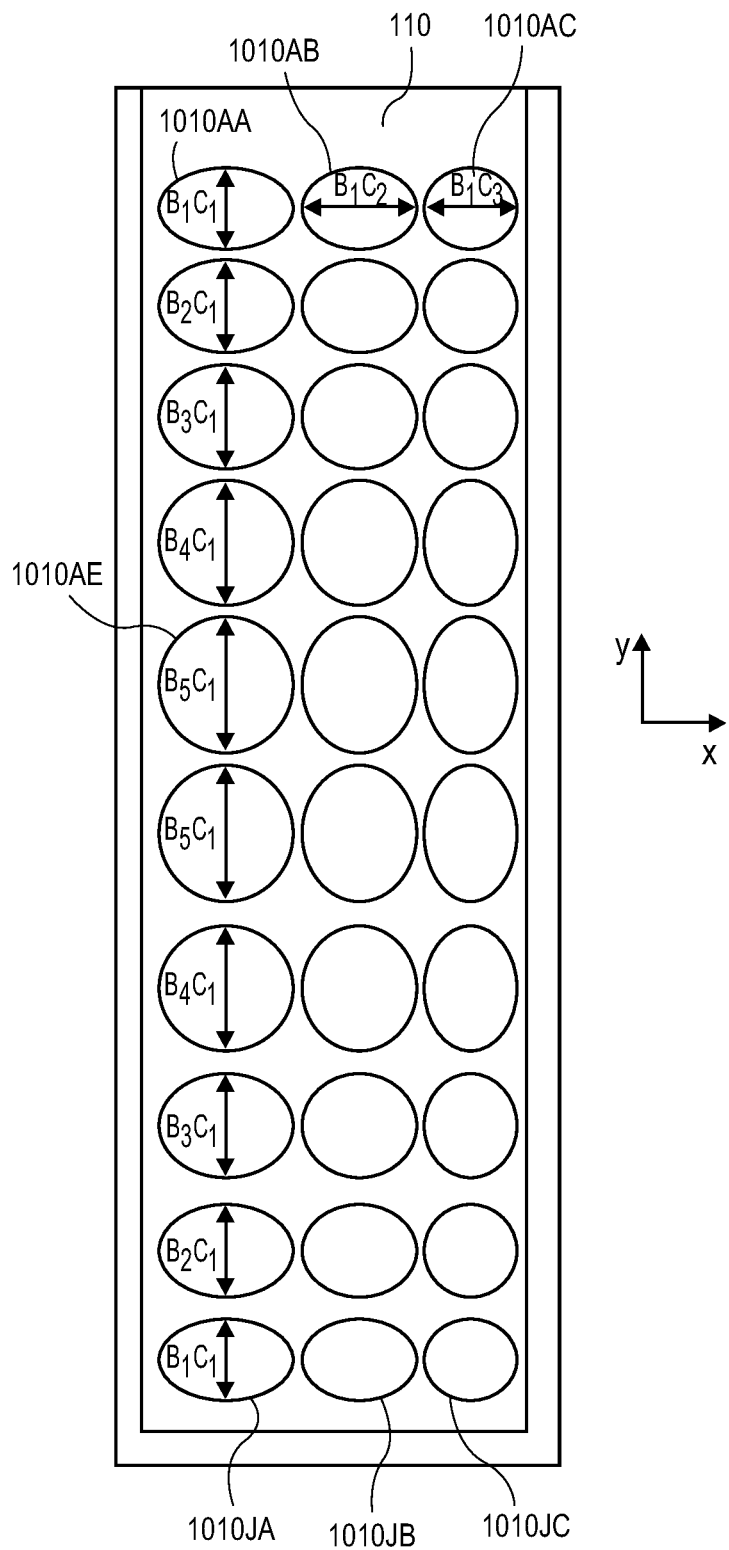
FIG. 1D is a plan view of a multi-mode MUT array with ellipsoidal transducer elements, in accordance with an embodiment.

Multi-mode array architecture may also be implemented with membranes of geometries other than circular/spheroidal. For example, FIG. 1D is a plan view of a multi-mode MUT array with ellipsoidal transducer elements, in accordance with an embodiment. Generally, ellipsoidal membranes are more readily driven into higher modes of oscillation as function of the disparity between the semi-principal axis B, C. By reducing the rotational symmetry from all rotation angles for a circular or spheroidal membrane down to only 2-fold symmetry (180°), mode shapes can be readily split into more distinct modes having separated resonant frequencies. Thus, piezoelectric membranes having different semi-principal axis dimensions provides an extra degree of freedom for shaping the frequency response of the transducer elements in a channel In a further embodiment, at least first and second semi-principal axes are sufficiently different lengths to provide a plurality of separate resonant frequencies (modes).

In the exemplary embodiment, the spatial arrangement of ellipsoidal membranes follows the same heuristics described in the context of the circular membranes, but with the exemplary ellipsoidal embodiment depicted in FIG. 1D, membrane dimensions are varied in both x and y dimensions within a channel population. As shown, only the length of a first semi-axis (e.g., B) is changed over a first dimension of a substrate while only the length of the second semi-axis (e.g., C) is changed over a second dimension of the substrate within a channel. As further illustrated in FIG. 1D, each axis is incrementally increased (and/or decreased) across one of the array dimensions to achieve a range of sizes within an RU that is greater than the difference in sizes between any two adjacent membranes. As shown, the B axis increments from $B_1$, up to $B_5$, and then back down to $B_1$ for elements 1010AA, 1010AE, 1010JA, respectively, along one dimension of the array (e.g., the y-axis of the substrate 101). The column or row comprising 1010AB-101JB and the column or row comprising 1010AC-1010JC have the same B axis increment as for the 1010AA-101JA column/row. The C axis in turn, increments with each element along a second dimension of the array (e.g., along the x-axis of the substrate 101) such that all elements of the row comprising 1010AA-1010JA are dimensioned to have an axis equal to $C_1$. Similarly, all elements of the row comprising 1010AB-1010JB are dimensioned to have an axis equal to $C_2$, and all elements of the row comprising 1010AC-1010JC are dimensioned to have an axis equal to $C_3$.

Figure 2A:
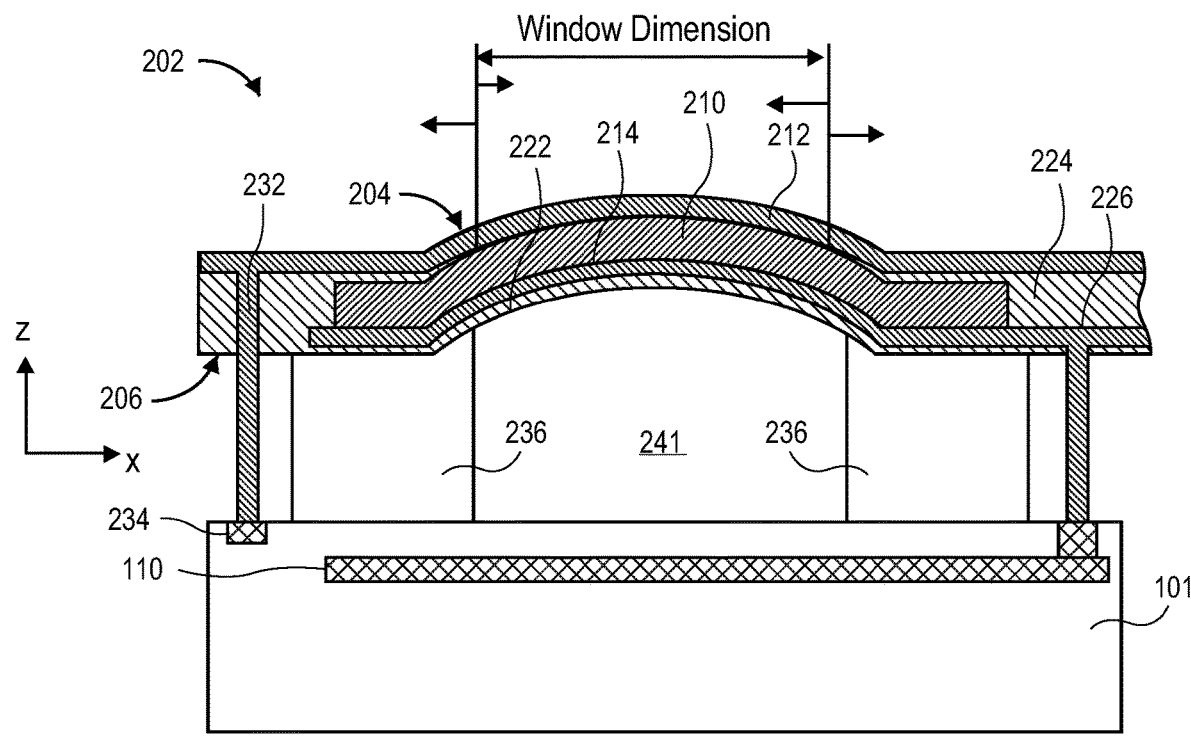
FIGS. 2A, 2B, and 2C are cross-sectional views of a piezoelectric transducer element which is utilized in the multi-mode MUT arrays of FIGS. 1A, 1B, and 1D, in accordance with embodiments.
Figure 2B:
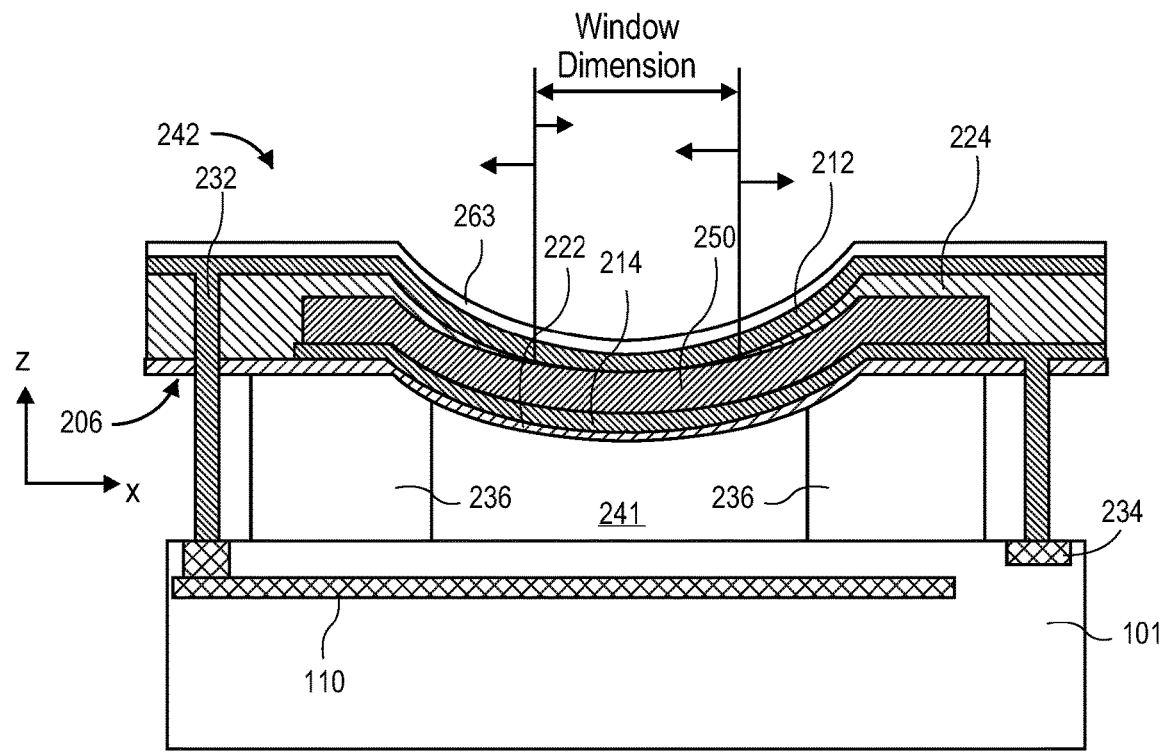
Figure 2C:
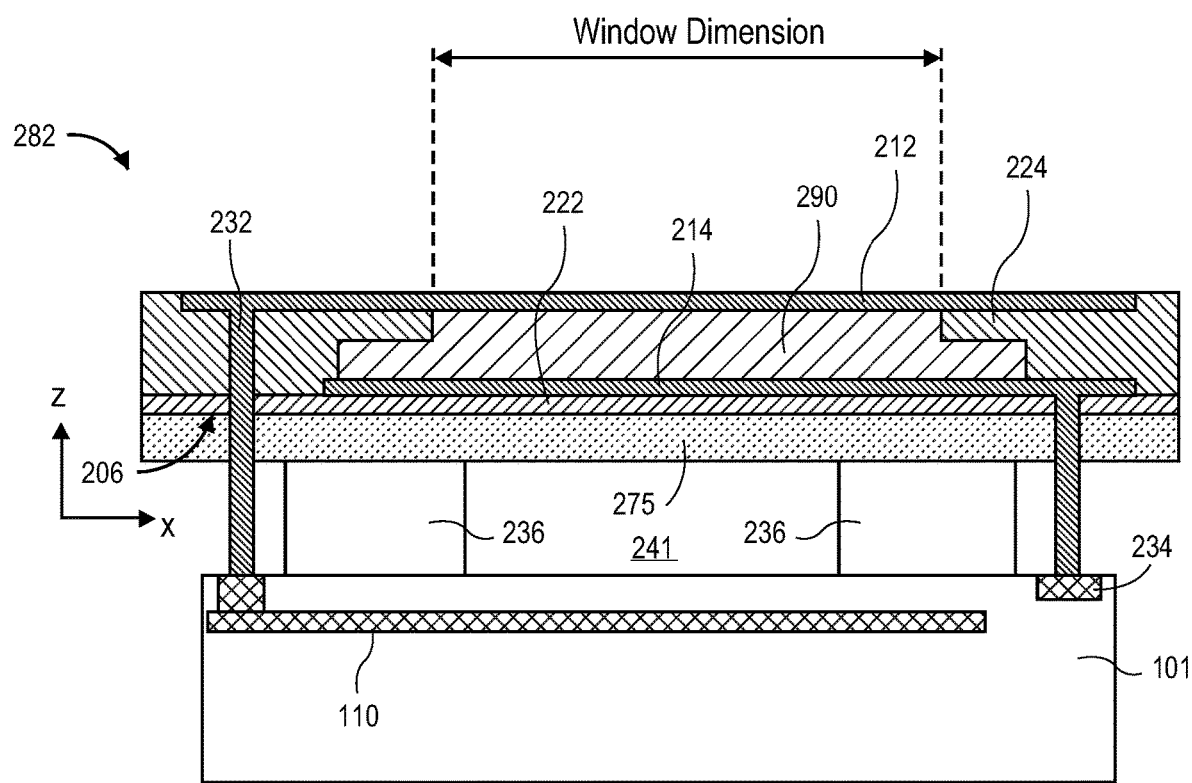

In embodiments, each transducer element of the dual-mode MUT array includes a piezoelectric membrane. The piezoelectric membrane may be a spheroid with curvature in a third (z) dimension to form a dome (as further illustrated by FIG. 2A), or a dimple (as further illustrated in FIG. 2B). Planar membranes are also possible, as further illustrated in FIG. 2C. In the context of FIGS. 2A-2C, exemplary micromachined (i.e., microelectromechanical) aspects of individual transducer elements are briefly described. It is to be appreciated that the structures depicted in FIGS. 2A-2C are included primarily as context for particular aspects of the present invention and to further illustrate the broad applicability of the present invention with respect to transducer element structure.

In FIG. 2A, a convex transducer element 202 includes a top surface 204 that during operation forms a portion of a vibrating outer surface of the pMUT array 100. The transducer element 202 also includes a bottom surface 206 that is attached to a top surface of the substrate 101. The transducer element 202 includes a convex or dome-shaped piezoelectric membrane 210 disposed between a reference electrode 212 and a drive/sense electrode 214. In one embodiment, the piezoelectric membrane 210 can be formed by depositing (e.g., sputtering) piezoelectric material particles in a uniform layer on a profile-transferring substrate (e.g., photoresist) that has a dome formed on a planar top surface, for example. An exemplary piezoelectric material is Lead Zirconate Titanate (PZT), although any known in the art to be amenable to conventional micromachine processing may also be utilized, such as, but not limited to polyvinylidene difluoride (PVDF) polymer particles, $BaTiO_3$, single crystal PMN-PT, and aluminum nitride (AlN). The drive/sense electrode and reference electrode 214, 212 can each be a thin film layer of conductive material deposited (e.g., by PVD, ALD, CVD, etc.) on the profile-profile transferring substrate. The conductive materials for the drive electrode layer can be any known in the art for such function, such as, but not limited to, one or more of Au, Pt, Ni, Ir, etc.), alloys thereof (e.g., AuSn, IrTiW, AuTiW, AuNi, etc.), oxides thereof (e.g., $IrO_2$, $NiO_2$, $PtO_2$, etc.), or composite stacks of two or more such materials.

Further as shown in FIG. 2A, in some implementations, the transducer element 202 can optionally include a thin film layer 222, such as silicon dioxide that can serve as a support and/or etch stop during fabrication. A dielectric membrane 224 may further serve to insulate the drive/sense electrode 214 from the reference electrode 212. Vertically-oriented electrical interconnect 226 connects the drive/sense electrode 214 to drive/sense circuits via the drive/sense electrode rail 110. A similar interconnect 232 connects the reference electrode 212 to a reference rail 234. An annular support 236, having a hole 241 with an axis of symmetry defining a center of the transducer element 202, mechanically couples the piezoelectric membrane 210 to the substrate 101. The support 236 may be of any conventional material, such as, but not limited to, silicon dioxide, polycrystalline silicon, polycrystalline germanium, SiGe, and the like. Exemplary thicknesses of support 236 range from 10-50 µm and exemplary thickness of the membrane 224 range from 2-20 µm.

FIG. 2B shows another example configuration for a transducer element 242 in which structures functionally similar to those in transducer element 202 are identified with like reference numbers. The transducer element 242 illustrates a concave piezoelectric membrane 250 that is concave in a resting state. Here, the drive/sense electrode 214 is disposed below the bottom surface of the concave piezoelectric membrane 250, while the reference electrode 212 is disposed above the top surface. A top protective passivation layer 263 is also shown.

FIG. 2C shows another example configuration for a transducer element 282 in which structures functionally similar to those in transducer element 202 are identified with like reference numbers. The transducer element 282 illustrates a planar piezoelectric membrane 290 that is planar in a resting state and unlike the element 202, 242, operates in bending mode and therefore further employs a membrane 275 (typically of silicon). Here, the drive/sense electrode 214 is disposed below the bottom surface of the planar piezoelectric membrane 290, while the reference electrode 212 is disposed above the top surface. An opposite electrode configuration from that depicted in each of FIGS. 2A-2C is also possible.

Figure 3A:
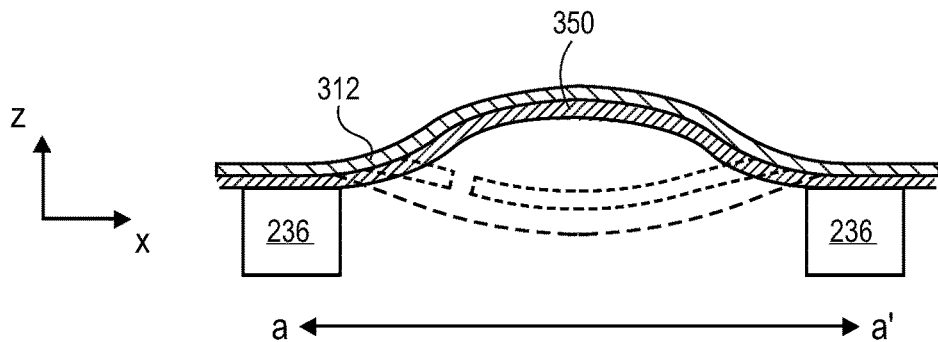
FIGS. 3A and 3B are cross-sectional schematics of a transducer element undergoing first and second modes of oscillation, in accordance with an embodiment.
Figure 3B:
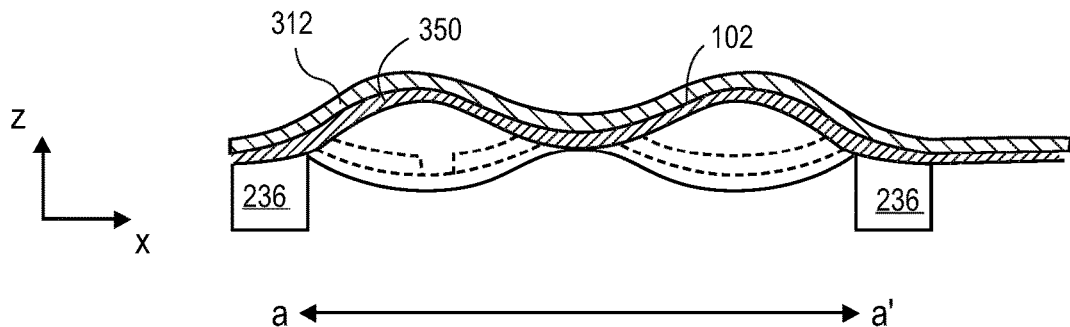
Figure 4A:
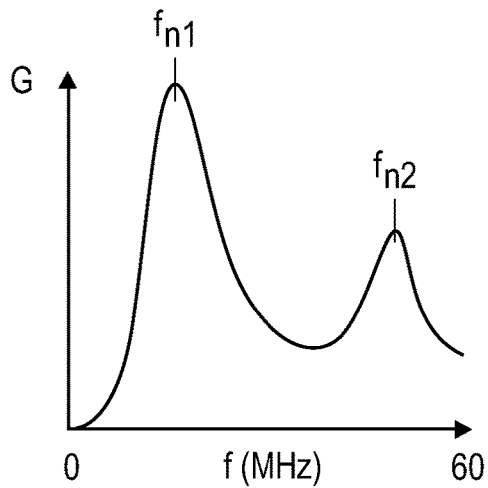
FIGS. 4A and 4B are frequency response graphs illustrating first and second resonant frequency bands associated with the first and second modes of oscillation depicted in FIGS. 3A and 3B, in accordance with an embodiment.
Figure 4B:
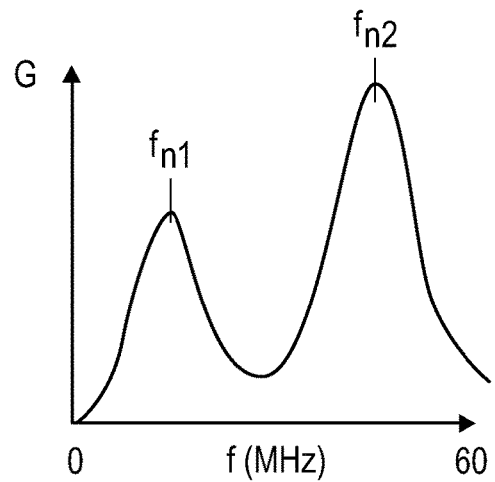

FIGS. 3A and 3B are cross-sectional schematics of a transducer element undergoing first and second modes of oscillation, in accordance with embodiments. FIGS. 4A and 4B are frequency response graphs illustrating first and second resonant frequency bands associated with the first and second modes of oscillation depicted in FIGS. 3A and 3B, in accordance with an embodiment. During operation, membranes within an array are induced into a first mode of vibration or oscillation having a characteristic first resonant frequency. Also during operation of the array, membranes within the array are induced into a second mode of vibration associated with a second resonant frequency, greater than that of the first resonant frequency. Both a first and second frequency band is then associated with a given population of different membrane sizes. FIG. 3A depicts, a cross-sectional view of a membrane 350 (which may be a piezoelectric material with planar, domed, or a cavity in a resting state) supported by supports 236 and driven by drive sense/ electrode 312 to provide a first mode of vibration when the drive sense/electrode pair 312 receives a time varying voltage drive signal. In FIG. 3B, the membrane oscillates in a second resonant as a result of a drive signal. Because the second mode of vibration is of a higher frequency (e.g., 2×) the fundamental, or first, mode of vibration, higher frequency regimes may be achieved in the higher mode. In the embodiments described herein (e.g., FIGS. 1A-1D), where circular (or ellipsoidal) membranes of differing size vibrate at various modes, two wide bands in the frequency response may be formed (e.g., first band and a second band at about twice the frequency of the first band). Considering that the piezoelectric excitation of a pMUT element is almost independent of the angle θ, advantageous mode shapes are the (0,1) mode, (0,2) mode, (0,3) mode in which the number of nodal diameter is 0.

FIGS. 4A and 4B are plots of performance metrics for the MUTs of FIGS. 3A and 3B, in accordance with embodiments. Referring to FIG. 4A, in one embodiment, a drive signal generator is to drive a first electrical signal to excite a first resonant mode ($f_{n1}$) of the membrane 350 more than a second resonant mode ($f_{n2}$). In FIG. 4B, the drive signal generator induces or excites the second resonant mode ($f_{n2}$) of the membrane 350 more than the first resonant mode ($f_{n1}$). Operation in either the first or high mode may be determined by at least a drive signal pulse width, and/or pulse shape, along with the membrane size and shape (e.g., circular vs. elliptical).

Figure 5:
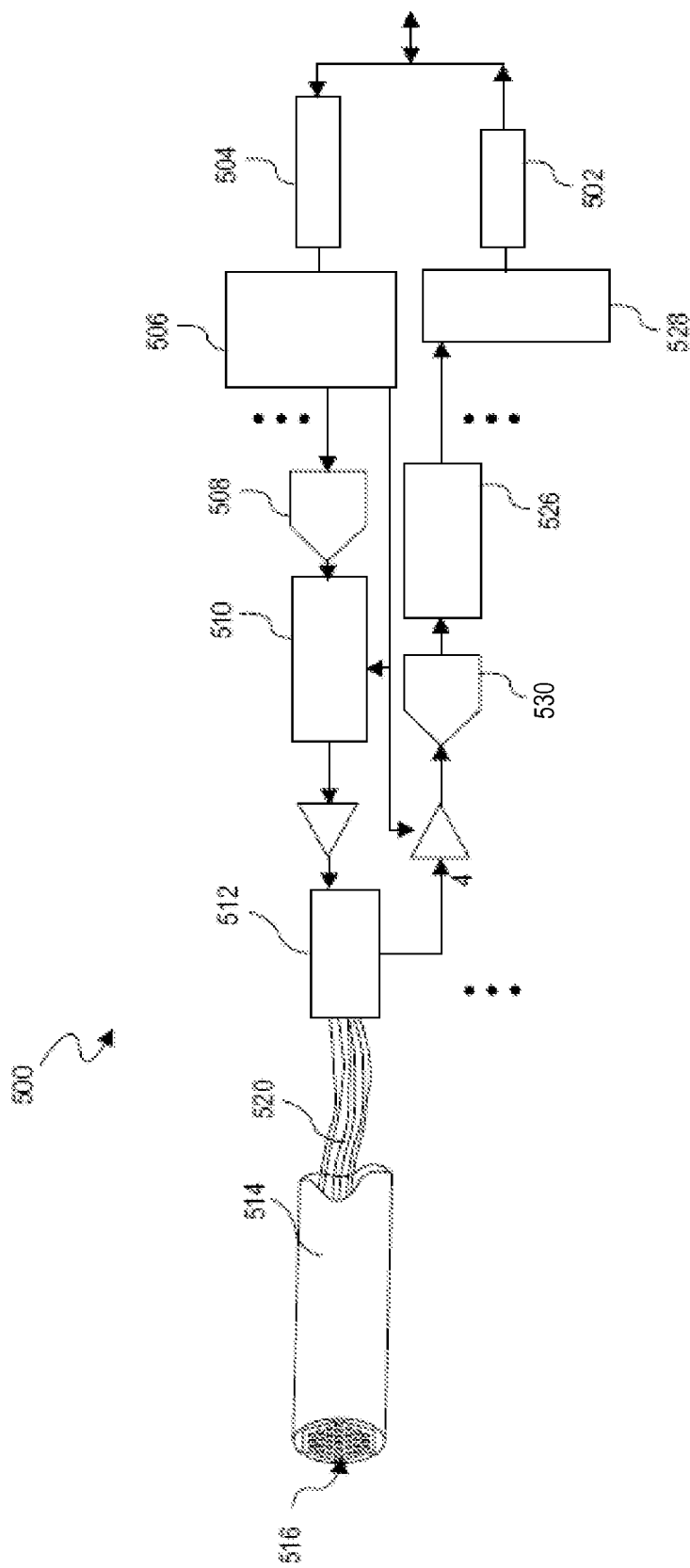
FIG. 5 is a functional block diagram of an ultrasonic transducer apparatus which employs a multi-mode MUT array, in accordance with an embodiment of the present invention.

FIG. 5 is a functional block diagram of an ultrasonic transducer apparatus 500 that employs a multi-mode MUT array, in accordance with an embodiment of the present invention. In an exemplary embodiment, the ultrasonic transducer apparatus 500 is for generating and sensing pressure waves in a medium, such as water, tissue matter, etc. The ultrasonic transducer apparatus 500 has many applications in which imaging of internal structural variations within a medium or multiple media is of interest, such as in medical diagnostics, product defect detection, etc. The apparatus 500 includes at least one multi-mode MUT array 516, which may have any of the multi-mode MUT array element designs described herein having any of the transducer element and element population attributes described. In exemplary embodiment, the MUT array 516 is a MUT housed in a handle portion 514 which may be manipulated by machine or by a user of the apparatus 500 to change the facing direction and location of the outer surface of the MUT array 516 as desired (e.g., facing the area(s) to be imaged). Electrical connector 520 electrically couple channels of the MUT array 516 to a communication interface external to the handle portion 514.

In embodiments, the apparatus 500 includes a signal generating means, which may be any known in the art, coupled to the MUT array 516, for example by way of electrical connector 520. The signal generating means is to provide an electrical drive signal to the drive/sense electrode of each channel in the array 516. In one specific embodiment, the signal generating means is to apply an electrical drive signal to cause the piezoelectric transducer element populations to resonate at frequencies between 1 MHz and 40 MHz. In an embodiment, the signal generating means includes a de-serializer 504 to de-serialize control signals that are then de-multiplexed by demux 506. The exemplary signal generating means further includes a digital-to-analog converter (DAC) 508 to convert the digital control signals into driving voltage signals for the individual transducer element channels in the MUT array 516. Respective time delays can be added to the individual drive voltage signal by a programmable time-delay controller 510 to beam steer, create the desired beam shape, focus, and direction, etc. Coupled between the pMUT channel connector 520 and the signal generating means is a switch network 512 to switch the MUT array 516 between drive and sense modes.

In embodiments, the apparatus 500 includes a signal collecting means, which may be any known in the art, coupled to the MUT array 516, for example by way of electrical connector 520. The signal collecting means is to collect and filter an electrical sense signal from the drive/ sense electrode channels in the MUT array 516. In one exemplary embodiment of a signal collecting means, an analog to digital converter (ADC) 530 is a receiver of voltage signals from channels the array 516, which are converted to digital signals. The digital signals may then be stored to a memory (not depicted) or passed directly to a signal processing means. An exemplary signal processing means includes a data compression unit 526 to compress the digital signals. A multiplexer 528 and a serializer 502 may further process (e.g., filter based on frequency, etc.) the received signals before relaying them to a memory, other storage, or a downstream processor, such as an image processor that is to generate a graphical display based on the received signals.

Figure 6:
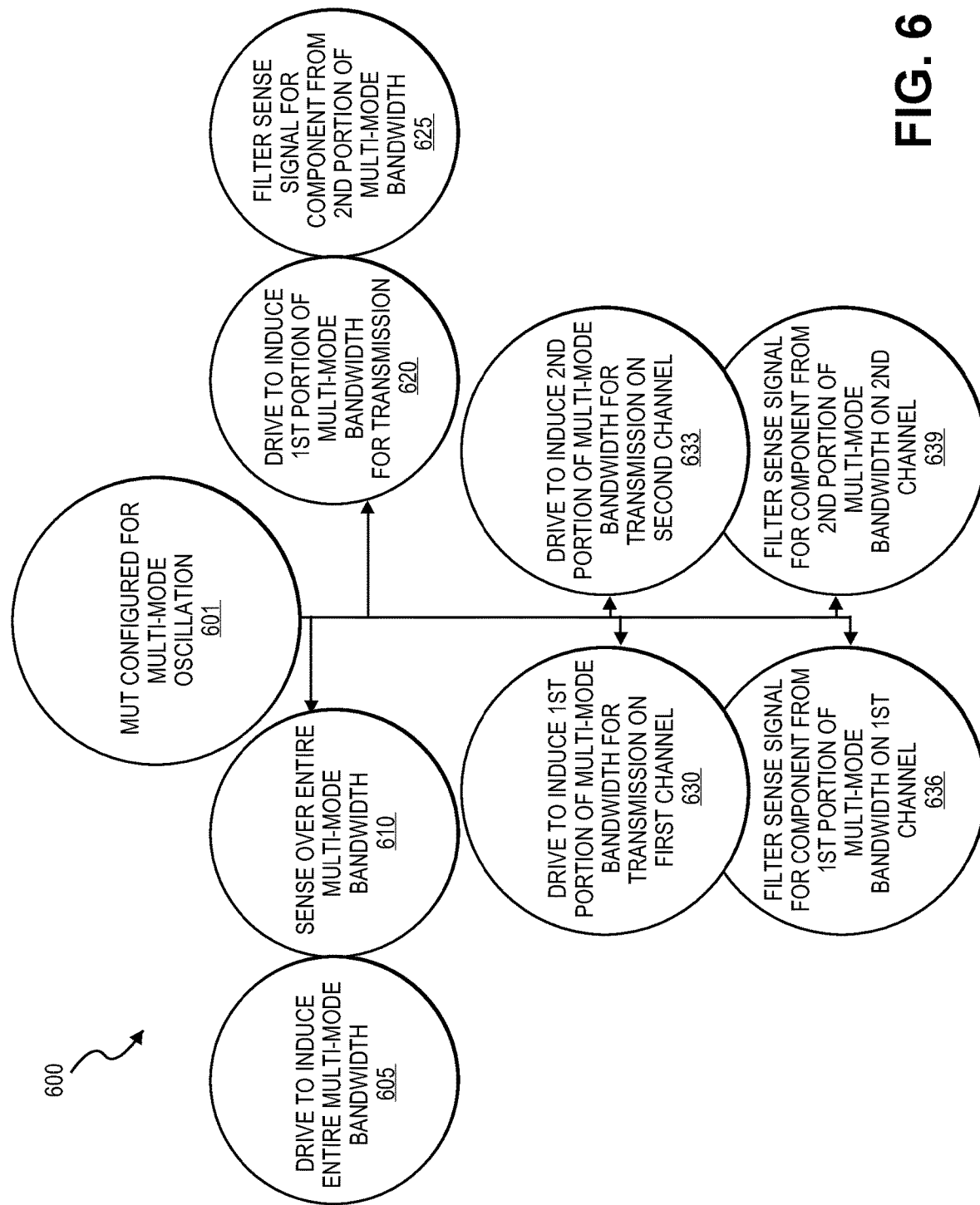
FIG. 6 is a flow diagram depicting modes of operation of a multi-mode MUT array, in accordance with embodiments.
Figure 7A:
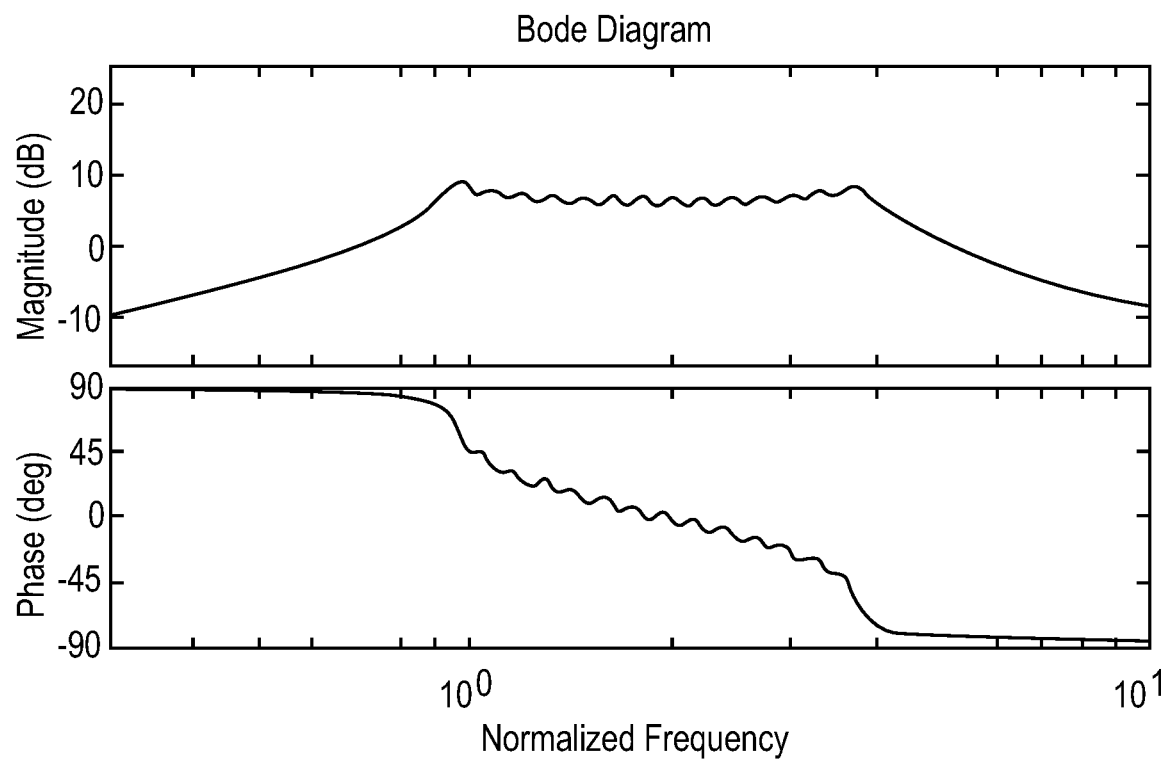
FIG. 7A is a modeled frequency response showing two bands corresponding to first and second vibrational modes of a MUT array, in accordance with an embodiment.
Figure 7B:
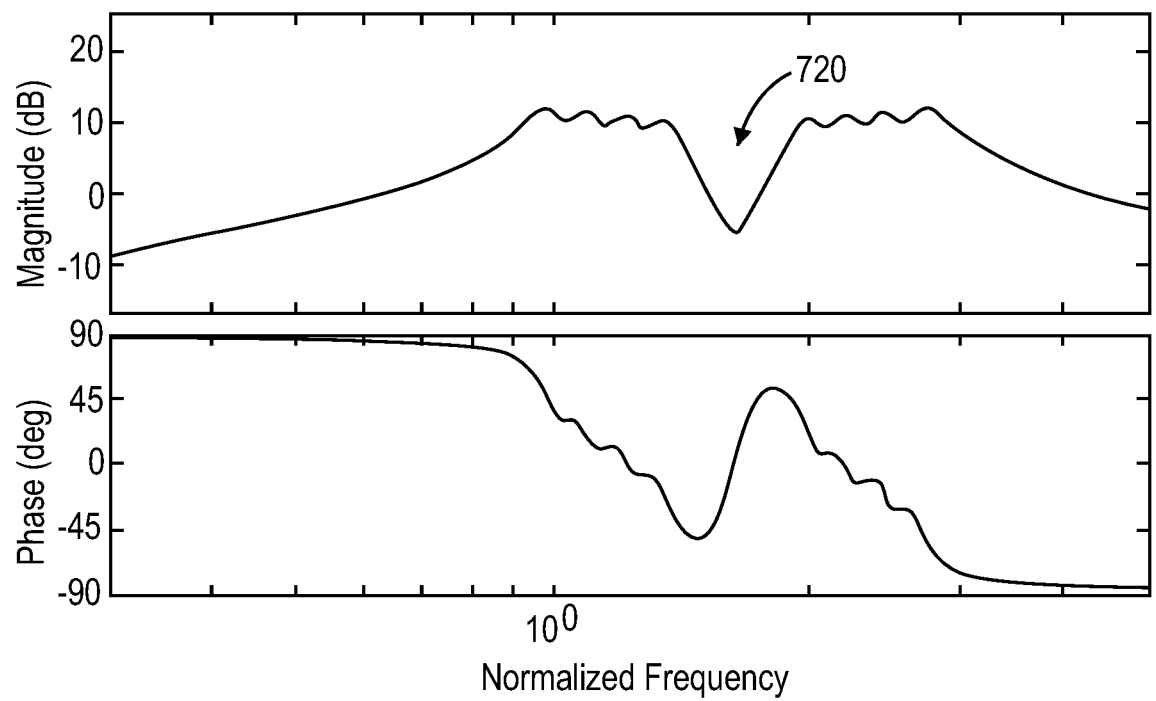
FIG. 7B a modeled frequency response for a MUT array suffering deconstructive phasing between first and second vibrational modes.

FIG. 6 is a flow diagram further depicting manners of operating a multi-mode MUT array, in accordance with embodiments. Generally, in the method 600 a multi-mode MUT array 601 is operated in at least one of three capacities. In the first, the multi-mode MUT array 601 is driven at operation 605 to induce the first and higher order modes concurrently to achieve a super-wide, multi-resonant frequency bandwidth. The multi-mode MUT array 601 is then further employed to sense over this entire bandwidth at operation 610. FIGS. 7A-7B describe this first manner of operation. In the second method of operating, the multimode MUT array 601 is driven to primary induce a first component of the multi-resonant frequency bandwidth for transmission at operation 620, while a second component the bandwidth is sensed at operation 625. FIGS. 8A-8C further describe this second manner of operating. In the third method, different channels of the multi-mode MUT array 601 are driven to induce different components of the multi-resonant frequency bandwidth (i.e., first and second resonant frequency bands) at operations 630, 633, and to sense the different components of the multi-resonant frequency bandwidth with the different channels at operation 636 and 639. This multi-signal or multi-channel mode is further described in the context of FIGS. 9A-9C.

In super-wide bandwidth embodiments, at least the first and second resonant modes overlap. Third and higher modes, if present, may also overlap with the bands of the next-higher and next-lower order. In the simplest case of two resonant modes, the highest resonance frequency of a first resonance frequency band associated with the first order mode is higher than the lowest resonance frequency of the second resonance frequency band, associated with the second order mode, as is depicted in the phase and magnitude graphs of FIG. 7A. For these super-wide bandwidth embodiments, the membrane population is designed, for example by controlling membrane size and layout as described in the context of FIGS. 1A-1D. Membrane effective mass, effective stiffness may also be controlled in the effort to avoid, or at least mitigate, destructive phasing.

Overlap between the highest resonance frequency of the first mode (associated with smallest membrane element) and the lowest resonance frequency of the second mode (associated with largest membrane element) may then merge both spectrum bands and extend the bandwidth of the array to at least 120%-6 dB fraction bandwidth (i.e., the −6 db bandwidth/center frequency). The challenge in overlapping resonance frequency bands due to variations in phase is illustrated by FIG. 7B, which is a modeled frequency response for a MUT array suffering some deconstructive phasing between first and second vibrational modes. For membranes of a fixed, uniform size for example, phase crosses zero between the first and second modes of vibration resulting in a notch in the frequency band at least significant as the notch 720 in FIG. 7B. It has been found however, that the resonant mode frequency bands can be fully merged by employing the gradual variation of element sizes depicted in FIG. 1B, for example. In this manner, a drive signal applied to a population of membranes of differing size within a same channel may induce both a first mode of oscillation in one or more membrane and also induce a second mode of oscillation in one or more other membranes. Likewise, the same bandwidth may be utilized in the sense cycle of the super-wide bandwidth pressure transducer.

Referring now to FIG. 8A, in the second manner of operating a multi-mode MUT a first frequency band primarily associated with a first mode of oscillation may be relied upon for transmission (Tx), while a second frequency band primarily associated with a second mode of oscillation may be relied upon for sensing. To operate in the mode illustrated in FIG. 8A, drive circuitry coupled to the multi-mode MUT array includes a signal generator that drives at least some of the transducer elements of a given channel with a first electrical signal that induces at least the first frequency band (e.g., lower band). The pulse width and shape, for example, may deviate from that employed for super-wide bandwidth embodiments to induce only a portion of the multi-resonant frequency band. Sense circuitry, on the other hand, includes a signal receiver coupled to the multi-mode MUT array to receive a second electrical signal from at least some of the transducer elements that includes a component from the second frequency band, which may be extracted with an appropriate band pass filter. Notably, when operating in this capacity, the resonance frequency bands may either overlap, or not. Where the bands do overlap, for example where the membrane dimensioning and layout follow the example of FIG. 1B and are also suitable for super-wide bandwidth operation, some membranes may oscillate in the second mode within the transmit frequency band and some membranes may oscillate in the first mode within the receive frequency band such that the Tx and Rx bands are not exclusive one resonant mode.

The second mode of operation illustrated in FIG. 8A is well-suited to the technique of tissue harmonic imaging (THI) where the first band of lower frequency vibration and the second band of higher frequency vibration are used without suffering the limitations in gain typical of lower bandwidth transducers. Generally, signal penetration in soft tissue increases as the transmit frequency is decreased, but there is a concomitant decrease in image resolution. As an ultrasound wave propagates through the target media, a change occurs in the shape and frequency of the transmitted signal due nonlinear distortion of the acoustic wave. Harmonic waves are generated within the media and build up with depth. The harmonic wave frequencies are higher integer multiples of the transmitted frequency much like the overtones of a musical notes. Current THI technology uses only the second harmonic (twice the transmitted frequency) for imaging. For example a transmit frequency of 3.0 MHz. which may provide maximum penetration, will return a harmonic frequency of 6.0 MHz. The returning higher frequency signal travels only in one direction to the probe. The advantages of high frequency imaging and the one-way travel effect include decreased reverberation, beam aberration, and side lobes, as well as increased resolution and cystic clearing.

As shown in FIG. 8B, transducer bandwidth may be a limiting factor for THI because the transducer must be both an efficient transmitter at one frequency and an efficient receiver at the second harmonic. Where transducer bandwidths (e.g., approximately 70%-80%-6 dB fractional bandwidth) are sub-optimal for harmonic imaging, the transmitted center frequency is typically set to 2/3 of the center frequency while the harmonic receive frequency is set to 4/3 of the center frequency. As further shown in dashed line of FIG. 8B, destructive interaction between elements of a channel may limit bandwidth so that gain (sensitivity) is reduced. However, as shown in FIG. 8C, the greater bandwidth of the multi-resonant mode MUT which includes both the first resonant mode and second resonant modes of a channel and encompassing the fundamental ($f_o$) and $2f_o$ frequencies naturally enable a very efficient THI transmitter and receiver, respectively. Therefore, THI can be advantageously implemented with the multi-mode MUT arrays having a combination of various membrane sizes (e.g., as depicted in FIG. 1B).

Figure 9A:
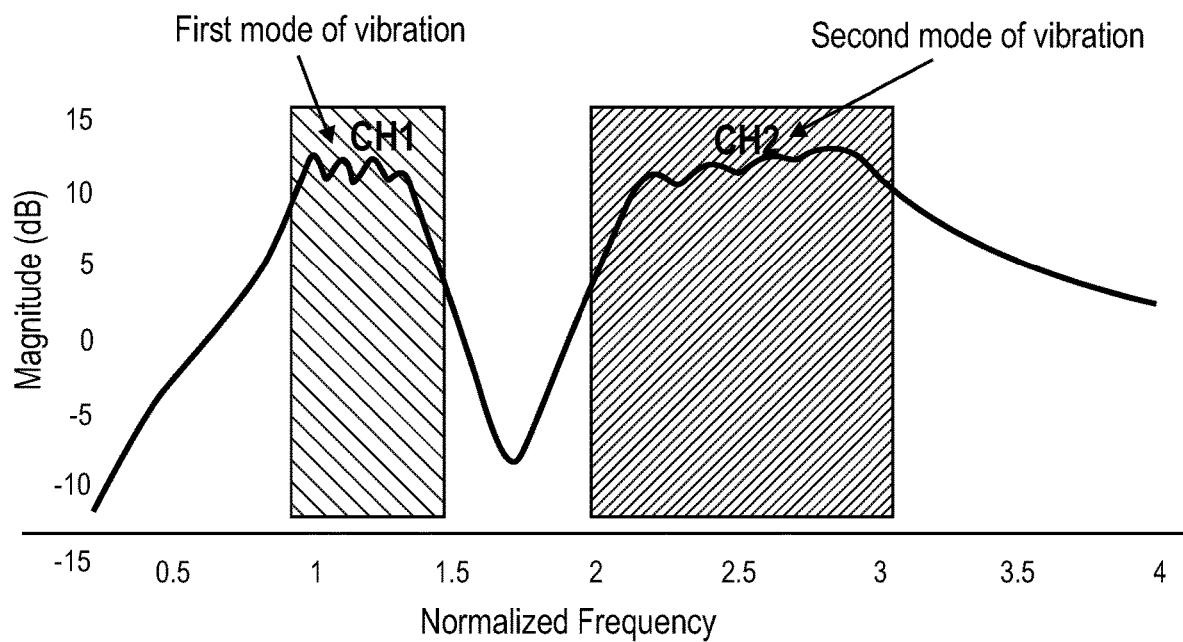
FIG. 9A is a modeled frequency response showing two bands corresponding to first and second vibrational modes of a MUT array, in accordance with an embodiment.

In embodiments, a multi-mode MUT array is operated in a third manner to further leverage the bandwidth associated with the multiple resonant modes by apportioning it across different channels of an ultrasonic transducer. A first frequency band, such as a lower frequency band associated primarily with a fundamental oscillation is employed in a first channel of the transducer while a second frequency band, such a higher frequency band associated primarily with a second or third order harmonic, is employed in a second channel to achieve a high sampling rate. In embodiments where all channels of a multi-mode MUT array are substantially identical and each channel including a plurality of elements having differing membrane sizes spatially distributed over the substrate following the heuristics exemplified by FIG. 1B, a first electrical signal of a first pulse shape and/or width (e.g., long) may induce a fundamental oscillation in one or more of the membranes in a first channel while a second electrical signal of a second pulse shape and/or width (e.g., short) may induce a higher order oscillation in one or more of the membranes in a second channel With the fundamental and higher order oscillations associated with low and high frequency bands, the modeled spectrum depicted in FIG. 9A is provided. During sense mode, the first and second channel signals are filtered with an appropriately different band pass, for example to extract the low frequency band from the first channel and the high frequency band from the second channel.

Figure 9B:
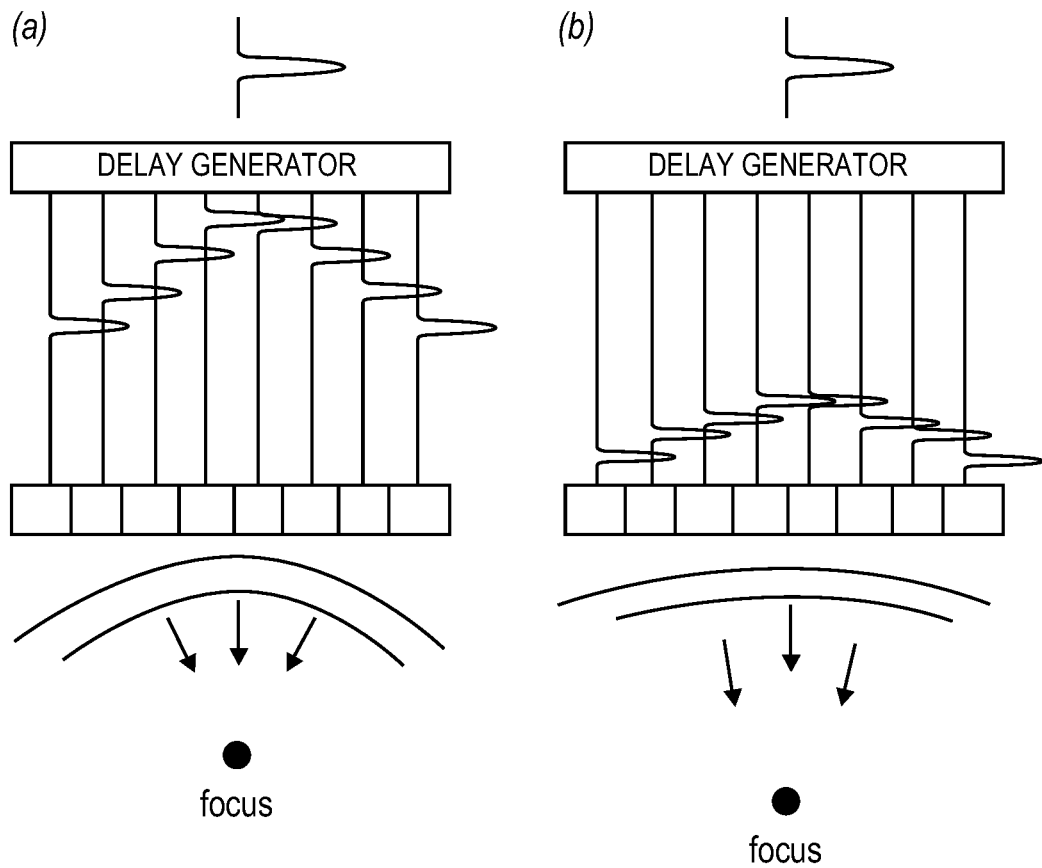
FIG. 9B illustrates a conventional multi-zone focus technique.
Figure 9B:
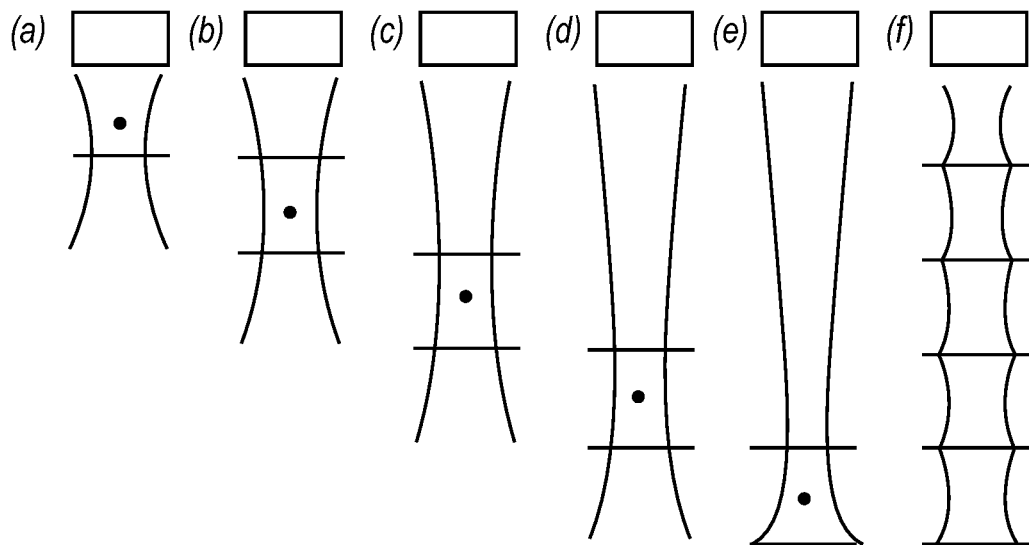
Figure 9C:
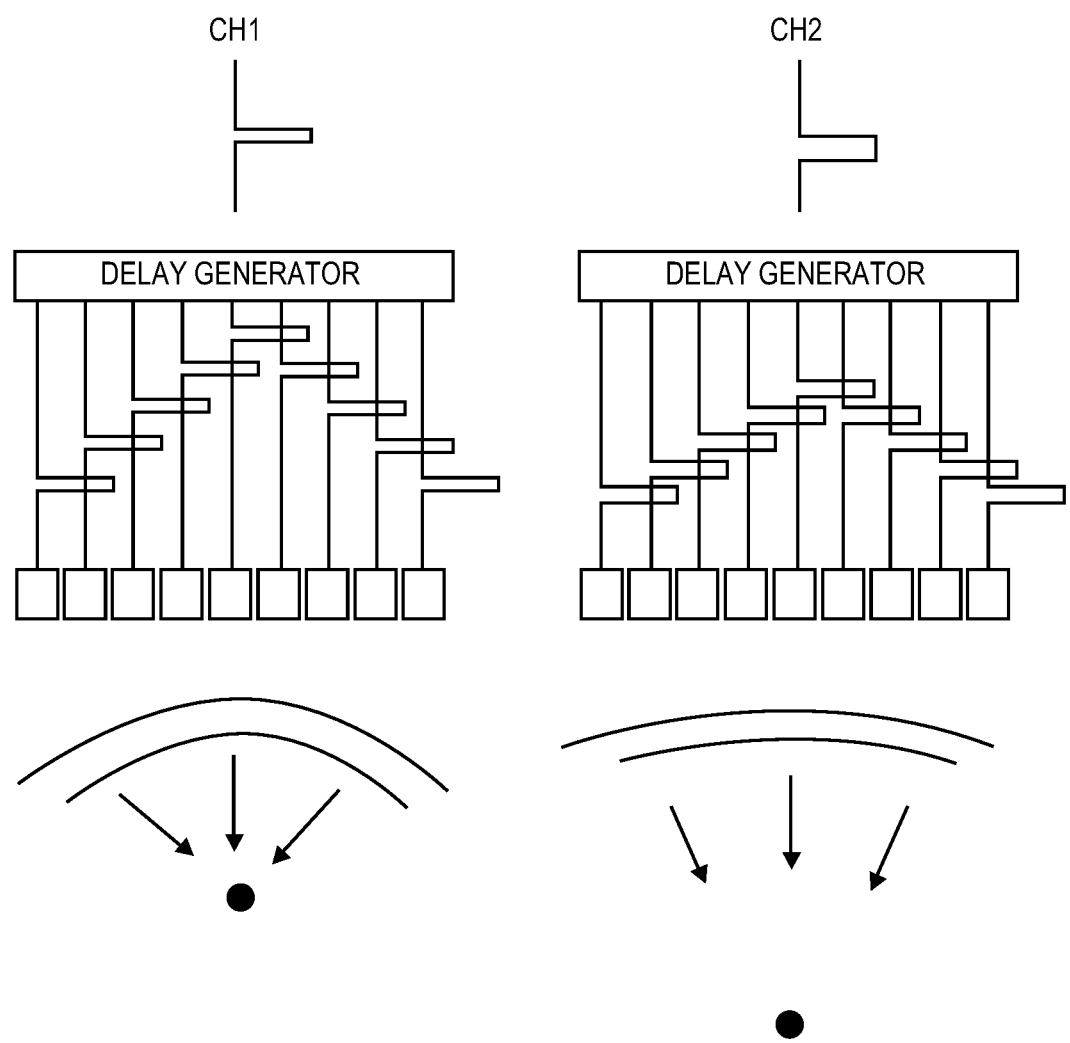
FIG. 9C illustrates a multi-zone focus technique, in accordance with a multi-channel embodiment.

Multi-channel operation may facilitate both a near field and far field focus zone (i.e., multi-depth) imaging at high sampling rates. Such a technique is in contrast to a conventional multi-zone focus technique, illustrated in FIG. 9B, where limited scanning rate leads to distorted images of fast moving objects such as the heart and flowing blood. Generally, scan rate is governed by the need to wait for the information to be returned from the most distant location before the next pulse is transmitted. As shown in FIG. 9B, to focus at a first depth a delay generator implements a first delay signature across a plurality of transducer channels. Then, a second pulse with different delay signature associated with a second depth is then sent. Where five depth zones are provided (a-f), five pulses and five sampling periods are needed, decreasing the scan rate further. In addition, a multiple focal zone technique is frequently used to improve the effective lateral resolution over the entire image depth. Within each zone a wide aperture/low f-number imaging is used to achieve improved resolution, and the images from each zone are stitched together. This will reduce the frame rate still more.

Where several wide bands may be formed in the frequency response as a result of different modes of vibration, for example in embodiments having an array such as is shown in FIG. 1B, each frequency band may be employed in an independent imaging channel Each channel can be excited by an excitation waveform at its associated frequency, such as a pulse with the duration of $(T \sim 1/2f_i)$ or chirp waveforms. The receive signal can be analyzed into various channels using corresponding band-pass filters or by various demodulation techniques. Consequently, the frame rate can be improved proportionally to the number of channels. As shown in FIG. 9C, the proposed multi-channel operational mode can efficiently implement a multiple focus zone technique where high frequency channels associated with a first excitation waveform of high frequency (short pulse) are used for a near field zone and focused accordingly (smaller focus length) to provide a high resolution image. Simultaneously, the LF (low frequency) channel (or channels) can be focused at deeper focus length to provide the maximum penetration. Theoretically, this approach provides the fast imaging rate of high-frequency transducers, deep penetration of low frequency transducers and improved effective lateral resolution over the entire image depth.

As noted elsewhere herein, one of the technical challenges to implementing multi-mode MUT embodiments described herein include destructive interference between membranes of a same channel. Frequency shaping with various sizes of vibrating membranes (flat, dome, dent) may be done to improve the bandwidth of the MUT and/or tailor the bandwidth to the particular modes of operation describe herein. Generally, the design task is then similar to designing a broadband bandpass filter by employing n first-order filters. While frequency shaping can be tuned by geometry using lithography as the shape of the frequency response is a function of the set of diaphragm diameters, several parameters including the effective stiffness, effective mass, natural resonance frequencies, the effective acoustic impedance and the coupling between elements are all strong functions of the membrane diameter. Consequently, the frequency spectrum of the transducer is a very complex function of the membrane diameters rendering the frequency shaping a potentially cumbersome and complex procedure in practice.

In embodiments therefore, a frequency response of a MUT array is optimized from a modeled nominal dimension by performing a sensitivity analysis on one or more mask levels of a MUT device. In the exemplary embodiment sensitivity analysis is performed using a single mask level that defines an area of contact between an electrode and material of the transducer membrane. In one advantageous embodiment, the single mask level is a dielectric window layer which defines a dimensioned opening over the membrane material through which an electrode makes contact. FIG. 2A, 2B, and 2C for example illustrate how a window dimension defines an opening in the dielectric membrane 224 (e.g., oxide) disposed between the piezoelectric membrane 210 and the drive/sense electrode 212. The dimension of this dielectric window is another parameter which primarily affects the amplitude of various mode shapes without significantly changing mode shapes and frequencies. Furthermore, it is expected to only slightly change the effective mass, effective stiffness and the effective acoustic impedance. As such, in embodiments a final frequency response a fine tuned based on the optimization of oxide window dimension.

Figure 10:
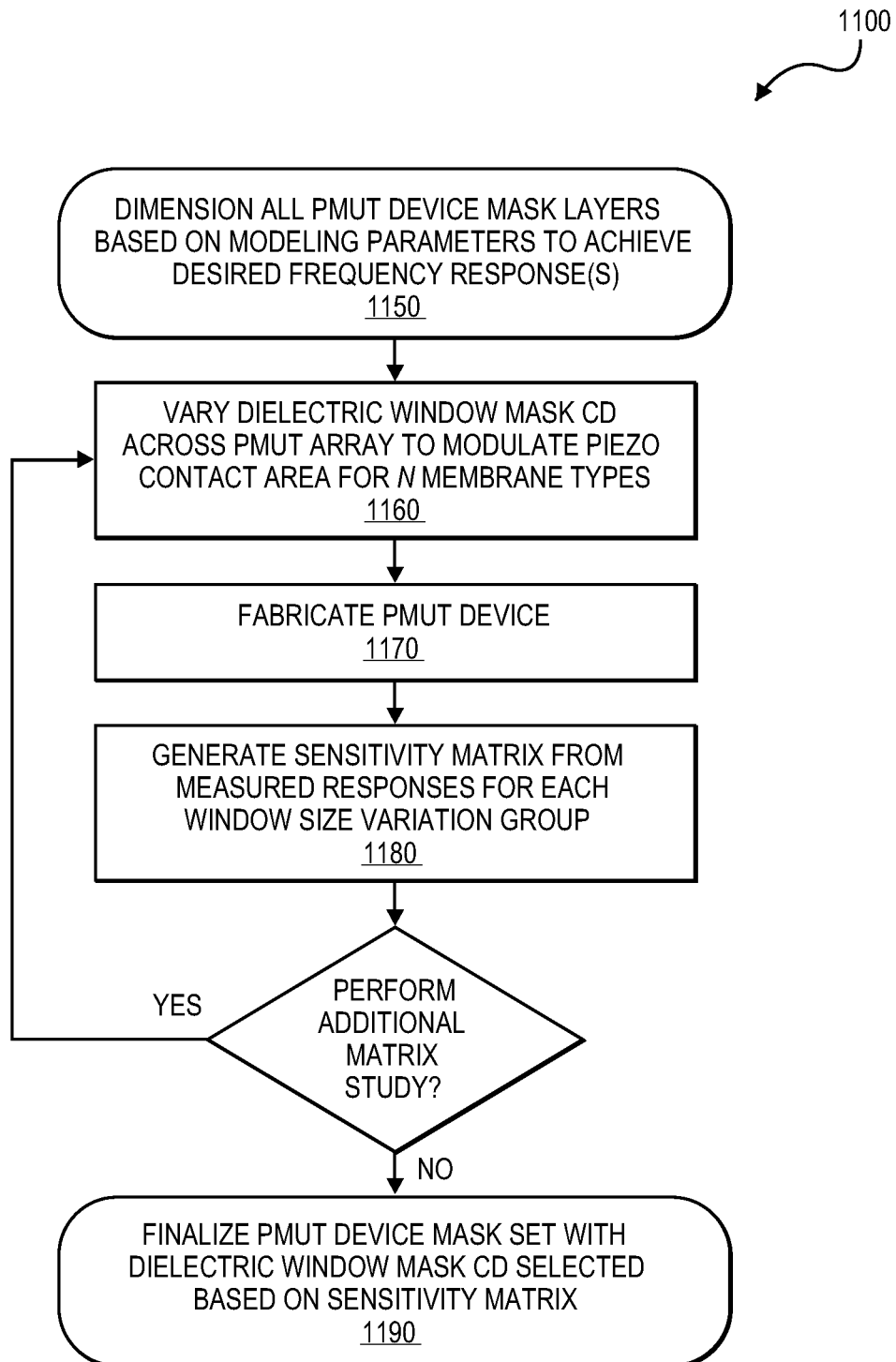
FIG. 10 is a flow diagram illustrating a method of optimizing a frequency response of a population of membranes having differing membrane sizes, in accordance with an embodiment.

An optimized window size can be estimated using numerical models (e.g. FEM models), or found experimentally. FIG. 10 is a flow diagram illustrating a method 1100 of optimizing a frequency shape from a population of membranes having differing membrane sizes by performing a sensitivity analysis of the dielectric windows size determined through experiment, potentially with only one fabrication run and one turn of a single mask layer (the window mask). The method 1100 begins at operation 1150 with dimensioning all mask layers of a PMUT device based on modeling parameters to achieve a desired nominal frequency response, or responses.

Figure 11:
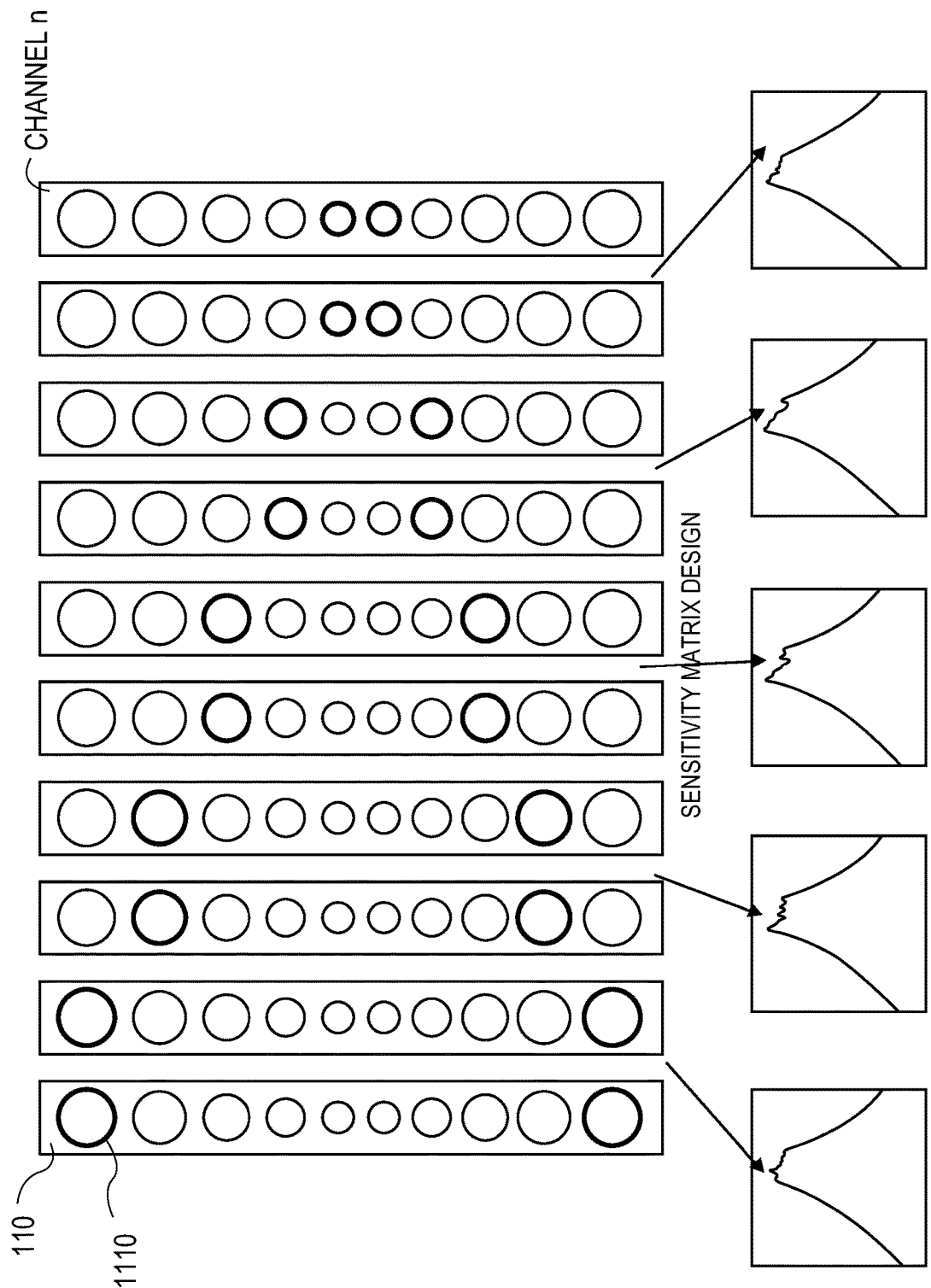
FIG. 11 is a plan view of a PMUT array with varied window sizes and corresponding response curves, in accordance with an embodiment.

At operation 1160, the dielectric window mask CD is varied across the PMUT array channels to modulate the piezoelectric contact area for n membrane types (sizes). For example, where a 1D ultrasound array includes 64-256 identical channels, each array can be designed as a sensitivity matrix by splitting these channels into n+1 groups: one control set estimated by the model and variations of the control set in which the oxide window of only one type of membrane per variation is changed by predefined value (2 μm-20 μm), as is further illustrated for 5 variations in FIG. 11. As shown, the circular band 1110 represents a window CD shrink, and for the channel associated with electrode rail 110, only the largest membrane element is modulated (shrunk) by the predetermined amount, while membranes of a different nominal size have a window size varied for the other four treatments depicted.

Returning to FIG. 10, at operation 1070 the PMUT device if fabricated using the mask set that includes the experimental window dimensioning. Channel responses (further illustrated in FIG. 11) are then measured for each window size variation from the fabricated device at operation 1180 (FIG. 10). These responses are then compared to responses associated with a nominal (modeled) dimension to generate the sensitivity terms $$\left(\frac{\partial y}{\partial x},\right.$$

where x is window size and y is frequency response). Optimal sizing of the window for each membrane size classification is then determined based on the sensitivity analysis to arrive at the desired final frequency response. A final mask set is then defined based on these optimal mask dimension determine for each different membrane size employed in the array at operation 1190. As further illustrated in FIG. 10, a second iteration of the sensitivity analysis may performed, as an option.

It is to be understood that the above description is illustrative, and not restrictive. For example, while flow diagrams in the figures show a particular order of operations performed by certain embodiments of the invention, it should be understood that such order may not be required (e.g., alternative embodiments may perform the operations in a different order, combine certain operations, overlap certain operations, etc.). Furthermore, many other embodiments will be apparent to those of skill in the art upon reading and understanding the above description. Although the present invention has been described with reference to specific exemplary embodiments, it will be recognized that the invention is not limited to the embodiments described.

What is claimed is:

1. A method of generating and sensing pressure waves in a medium, the method comprising:
    driving an electrode of at least some transducer elements of a micromachined ultrasonic transducer (MUT) array with a first electrical signal wherein, for each transducer element of the MUT array;
        a membrane of each transducer element of a plurality of transducer elements of the MUT array is dimensioned to enter a respective first mode of oscillation of a plurality of modes of oscillation, the respective first mode of oscillation corresponding to a solution of a respective Bessel function, wherein the respective first mode of oscillation corresponds to a respective first resonant frequency in a first frequency band; and wherein the membrane of each transducer element of the plurality of transducer elements of the MUT array is dimensioned to enter a respective second mode of oscillation of the plurality of modes of oscillation, the respective second mode of oscillation corresponding to a solution of a respective Bessel function, wherein the respective second mode of oscillation corresponds to a respective second resonant frequency in a second frequency band, wherein the respective first mode of oscillation and the respective second mode of oscillation are different respective modes of oscillation, and wherein the respective second resonant frequency is greater than the respective first resonant frequency, wherein the first electrical signal induces at least the respective first mode of oscillation associated with the first resonant frequency band; and
    receiving a second electrical signal from the electrode that includes at least a component corresponding to the respective second mode of oscillation associated with the second resonant frequency band.

2. The method of claim 1, wherein the driving induces both the first frequency band and the second frequency band; and wherein the second electrical signal includes components from both the first and second frequency bands.

3. The method of claim 2, wherein the first frequency band is induced on a first channel of the array and the second frequency band is induced on a second channel of the array; and
    wherein components from the first frequency band are collected from the first channel and the components from the second frequency band are collected from the second channel.

4. The method of claim 1, wherein the first electrical signal has a pulse width and shape that preferentially induces the first band more than the second band; and wherein the signal receiver is to filter a component of the second electrical signal associated with the second band from that associated with the first band.

* * * * *